US011328816B2

(12) United States Patent
Crego et al.

(10) Patent No.: US 11,328,816 B2
(45) Date of Patent: May 10, 2022

(54) SYSTEMS AND METHODS FOR DENTAL PRACTICE PLANNING AND MANAGEMENT

(71) Applicant: Spear Education, LLC, Scottsdale, AZ (US)

(72) Inventors: Matthew M. Crego, Peoria, AZ (US); Mitchell Ward Ellingson, Phoenix, AZ (US); Yonas Yohannes, Peoria, AZ (US)

(73) Assignee: SPEAR EDUCATION, LLC, Scottsdale, AZ (US)

( * ) Notice: Subject to any disclaimer, the term of this patent is extended or adjusted under 35 U.S.C. 154(b) by 254 days.

(21) Appl. No.: 16/503,192

(22) Filed: Jul. 3, 2019

(65) Prior Publication Data

US 2019/0326011 A1    Oct. 24, 2019

Related U.S. Application Data

(63) Continuation of application No. PCT/US2018/012378, filed on Jan. 4, 2018.
(Continued)

(51) Int. Cl.
*G16H 40/20* (2018.01)
*G06Q 10/10* (2012.01)
(Continued)

(52) U.S. Cl.
CPC ............ *G16H 40/20* (2018.01); *G06Q 10/10* (2013.01); *G06Q 50/10* (2013.01); *G16H 40/40* (2018.01); *G16H 50/20* (2018.01)

(58) Field of Classification Search
CPC ........ G16H 10/60; G16H 15/00; G16H 40/20; G16H 50/20; G16H 50/30; G16H 50/70; G16H 40/63; G16H 30/20; G16H 40/40; G06N 20/00; G06N 3/08; G06N 5/022; G06Q 10/10; G06Q 50/10
See application file for complete search history.

(56) References Cited

U.S. PATENT DOCUMENTS

2005/0192835 A1  9/2005  Kuo et al.
2008/0033754 A1  2/2008  Smith et al.
(Continued)

FOREIGN PATENT DOCUMENTS

WO    2018129184    7/2018

OTHER PUBLICATIONS

Office Action dated Apr. 26, 2021 in Canadian Patent Application No. 3,049,412.
(Continued)

*Primary Examiner* — Maroun P Kanaan
(74) *Attorney, Agent, or Firm* — Snell & Wilmer L.L.P.

(57) ABSTRACT

System and methods for the integration of dental practice management systems are disclosed herein. The systems and methods may generate models (including schedule models and financial models) from the data provided by a plurality of dental practices. These models can be used to quantitatively evaluate the efficiency and other operating characteristics of a particular dental practice, and can identify operational issues within the practice. Further, the systems and methods can evaluate metrics of the dental practice against goal metrics and/or standard metrics, and recommend and implement solutions based on the comparison.

20 Claims, 17 Drawing Sheets

Related U.S. Application Data

(60) Provisional application No. 62/442,907, filed on Jan. 5, 2017.

(51) Int. Cl.
    *G16H 50/20*     (2018.01)
    *G16H 40/40*     (2018.01)
    *G06Q 50/10*     (2012.01)

(56) References Cited

U.S. PATENT DOCUMENTS

| | | |
|---|---|---|
| 2010/0105009 A1 | 4/2010 | Karkar et al. |
| 2012/0016792 A1* | 1/2012 | Fontenot ............... G06Q 40/00 705/38 |
| 2013/0144647 A1 | 6/2013 | Ellingson |
| 2015/0019252 A1 | 1/2015 | Dawson et al. |
| 2015/0178684 A1 | 6/2015 | Krumel et al. |
| 2016/0092641 A1* | 3/2016 | Delaney ............... G16H 10/60 705/3 |

OTHER PUBLICATIONS

International Search Report in the International Application No. PCT/US2018/012378 dated May 8, 2018.
Written Opinion of the International Searching Authority in the International Application No. PCT/US2018/012378 dated May 8, 2018.
International Preliminary Report in Patentability in the International Application No. PCT/US2018/012378 dated Jul. 9, 2019.

* cited by examiner

FIG. 5

SYSTEMS AND METHODS FOR DENTAL PRACTICE PLANNING AND MANAGEMENT

CROSS REFERENCE TO RELATED APPLICATIONS

This application is continuation of PCT Application No. PCT/US2018/012378, filed on Jan. 4, 2018 entitled "SYSTEM AND METHODS FOR DENTAL PRACTICE PLANNING AND MANAGEMENT," which claims priority to U.S. provisional patent application No. 62/442,907, filed on Jan. 5, 2017 entitled "SYSTEM AND METHODS FOR DENTAL PRACTICE PLANNING AND MANAGEMENT," both of which are incorporated by reference herein in their entireties.

FIELD

The present disclosure relates to systems for resource management and analysis of dental practices.

BACKGROUND

Dental practices typically utilize one or more software and/or hardware systems to manage various aspects of the practices. Billing, scheduling, and expense management, for example, are frequently managed using computer-based solutions. However, utilizing multiple individual or distinct systems for various aspects of dental practice management can be inefficient and potentially expensive. A unified computer-based solution may provide increased efficiency and/or reduced cost.

Further, to improve efficiency, many dental practices seek professional advisement, such as from a dental management consultant. Consultants may analyze various aspects of a dental practice to determine areas of potential improvement. It may be beneficial for dental practices and consultants to have access to data and data models of similar dental practices, which would allow for direct comparison of the performance of a particular dental practice with the performance of similar practices.

SUMMARY

Systems, methods, and computer readable medium (collectively, the "system") are disclosed for managing dental practices. The systems may generate financial and schedule data from a first user system, and a financial model and a schedule model from data received from a plurality of user systems utilized by dental practices having a shared characteristic to the first user system. The systems may compare the financial data to the revenue model and the schedule data to the schedule model.

In various embodiments, the systems comprise an application server, a formatted database, and a data processing module. The systems may further comprise a consultant user interface in communication with at least one of the formatted database and the data processing module. The consultant user interface may determine which data is transmitted from the application server to the first user system.

The forgoing features and elements may be combined in various combinations without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may be obtained by referring to the detailed description and claims when considered in connection with the drawing figures, wherein like numerals denote like elements.

FIG. 5 illustrates a graphical user interface of the software application of FIG. 4, in accordance with various embodiments;

DETAILED DESCRIPTION

The detailed description of various embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment.

Figure 1A:
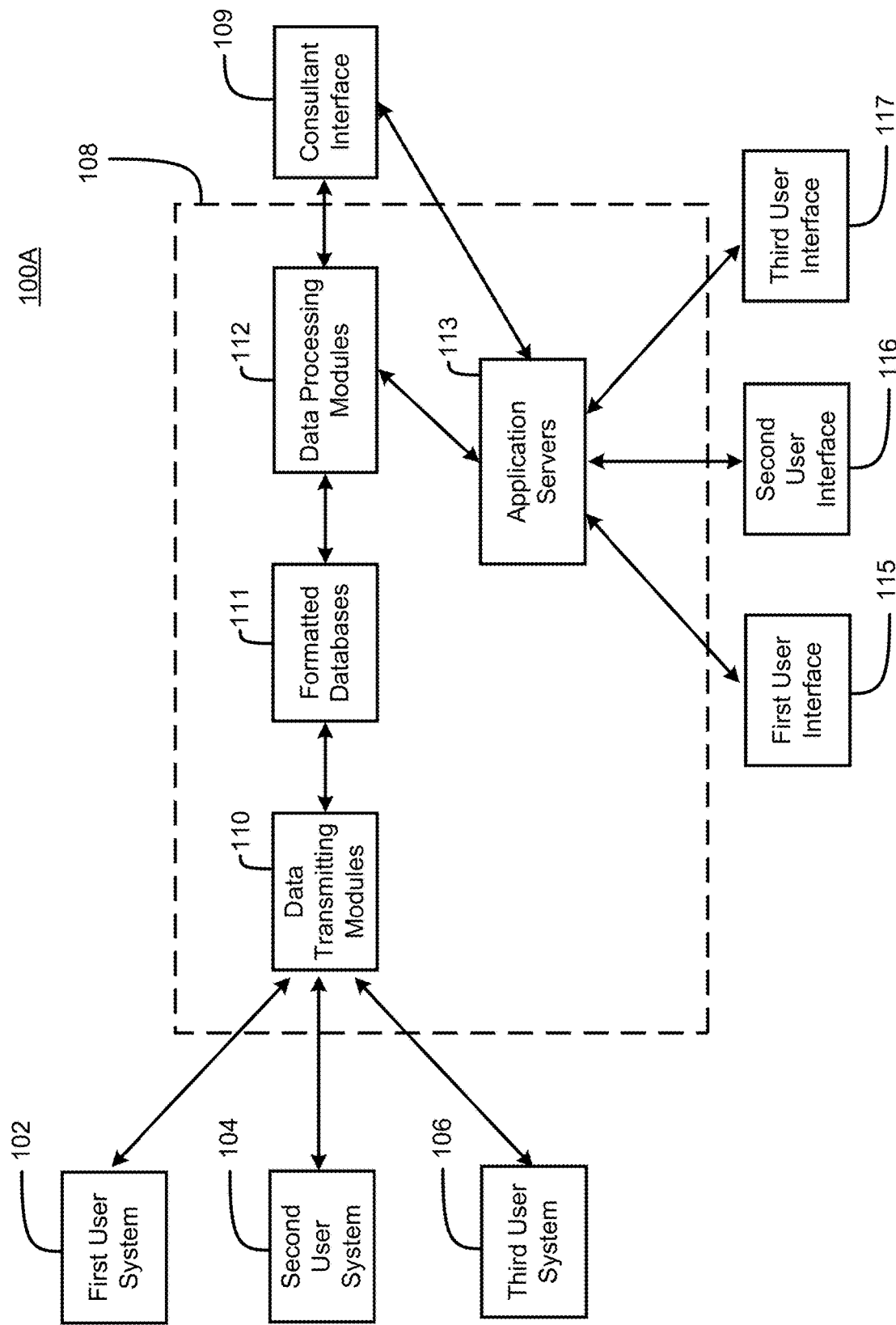
FIG. 1A illustrates a system for dental practice planning and management, in accordance with various embodiments.
Figure 1B:
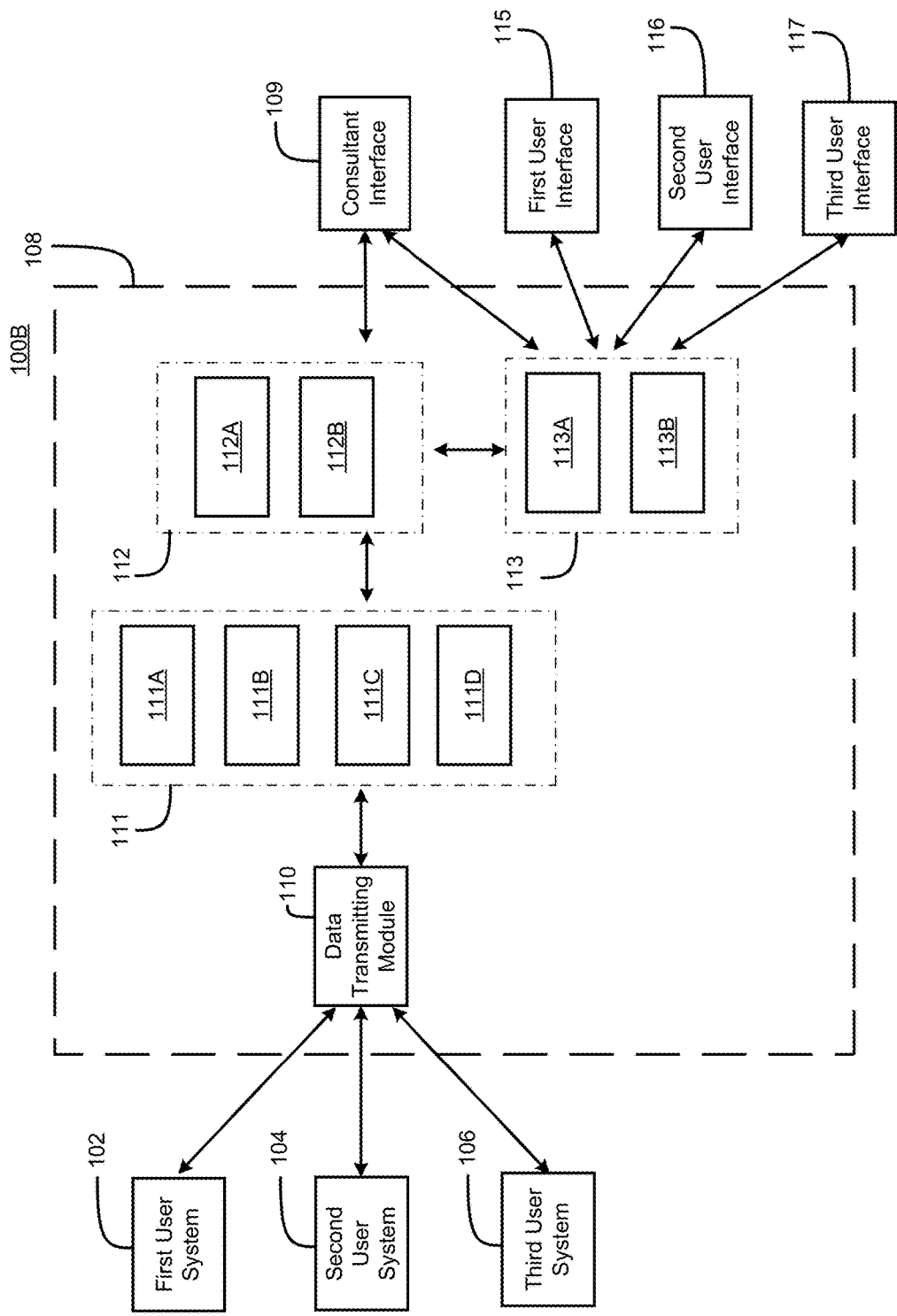
FIG. 1B illustrates another system for dental practice planning and management, in accordance with various embodiments.

The present disclosure provides systems, methods, and computer program products for managing dental practices, although the systems described herein are envisioned as applying to medical practices, legal practices, and any other professional practices. With reference to FIGS. 1A and 1B, systems 100A and 100B, respectively, are shown, in accordance with various embodiments. Systems 100A and 100B may comprise a first user system 102 running a native application and/or a web browser. First user system 102 may comprise any system or device capable of receiving, storing, manipulating, and/or displaying electronic data. For example, first user system 102 may take the form of a computer or processor, or a set of computers/processors, although other types of computing units or systems may be used, including laptops, notebooks, hand held computers, personal digital assistants, cellular phones, smart phones (e.g., iPhone®, BlackBerry®, Android®, etc.), tablets, wearables (e.g., smart watches and smart glasses), or any other device capable of receiving and displaying electronic data.

In various embodiments, first user system 102 is utilized by one or more employees of a dental practice, for the purposes of entering data related to the operation of the dental practice. For example, first user system 102 can comprise a computer system into which employees of the dental practice input data such as patient data, scheduling data, billing data, financial data (including, among others, revenue data and/or expense data), and any other data relevant to the operation of the dental practice. First user system 102 may comprise, for example, one or more software applications that facilitate the entry and storage of relevant data. Such software applications can comprise, for example, billing software, patient management software, accounting software, and scheduling software, among others.

First user system 102 can comprise, for example, a dental practice management system ("DPMS") which stores data input by various employees of the dental practice in a particular and/or proprietary format. In that regard, each DPMS may have a different schema and/or structure in which data is stored. For example, first user system 102 may include a DPMS that stores relevant data in a relational database within first user system 102 comprising various tables related by keys. The DPMS of first user system 102 can be local (i.e., a program stored within and executed by a local computer), cloud-based, or any other configuration that allows for receiving, storing, and manipulating data of the dental practice.

In various embodiments, first user system 102 and/or applications running on the system may communicate with a dental integration platform (DIP) 108. For example, first user system 102 can transmit data relevant to the operation of the dental practice to DIP 108, and the data can be transformed, formatted, stored, and processed by DIP 108.

In various embodiments, data stored within a database of a DPMS utilized by first user system 102 is provided to DIP 108.

First user system 102 and DIP 108 may, for example, communicate over a network. As used herein, the term "network" includes any cloud, cloud computing system or electronic communications system or method which incorporates hardware and/or software components. Communication among the various systems may be accomplished through any suitable communication channels, such as, for example, a telephone network, an extranet, an intranet, Internet, online communications, satellite communications, off-line communications, wireless communications, local area network (LAN), wide area network (WAN), virtual private network (VPN), networked or linked devices and/or any suitable communication or data input modality. Moreover, although the systems described herein may typically be implemented with TCP/IP communications protocols, the system may also be implemented using IPX, Appletalk, IP-6, NetBIOS, OSI, any tunneling protocol (e.g. IPsec, SSH), or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, Dilip Naik, Internet Standards and Protocols (1998); Java 2 Complete, various authors, (Sybex 1999); Deborah Ray and Eric Ray, Mastering HTML 4.0 (1997); and Loshin, TCP/IP Clearly Explained (1997) and David Gourley and Brian Totty, HTTP, The Definitive Guide (2002), the contents of which are hereby incorporated by reference.

A network may be unsecure. Thus, communication over the network may utilize data encryption. Encryption may be performed by way of any of the techniques now available in the art or which may become available—e.g., Twofish, RSA, El Gamal, Schorr signature, DSA, PGP, PKI, GPG (GnuPG), and symmetric and asymmetric cryptosystems.

In various embodiments, one or more components of DIP 108 can comprise cloud-based modules and/or components. As will be described in further detail, components of DIP 108 such as data transmitting modules, databases, data processing modules, application servers, and interfaces can be cloud-based components. Although they are described and illustrated as discrete components, one or more of the components of DIP 108 can be combined with one another, or distributed among one or more cloud-based computing systems.

In various embodiments, first user system 102 comprises an application configured to transmit data from first user system 102 to DIP 108. For example, first user system 102 may comprise an upload application programming interface (API) which transmits data to DIP 108. The upload API can transmit data from first user system 102 to DIP 108 in response a request from DIP 108, or the upload API can be programmed to transmit data to DIP 108 under predetermined circumstances, including at or during a particular time or interval of time. Any manner of transmitting data from first user system 102 to DIP 108, including any software or hardware, is within the scope of the present disclosure.

In various embodiments, DIP 108 comprises a data transmitting module 110. For example, data transmitting module 110 may receive data transmitted from first user system 102 to DIP 108. Data transmitting module 110 may be in communication with a formatted database 111, and may transmit data received from first user system 102 to formatted database 111.

Data transmitting module 110 may, for example, comprise a conversion engine configured to receive data from first user system 102 and format the data for storage within formatted database 111. For example, data transmitting module 110 can receive the data transmitted by the DPMS of first user system 102 and transmit it for storage within formatted database 111.

With reference to FIG. 1B, system 100B can comprise multiple formatted databases 111. For example, system 100B can comprise a system database 111A, a periodic trend database 111B, an issue database 111C, a content database 111D, or any combination of multiple databases, including multiple databases of the same type. Databases, such as databases 111A-111D, can comprise SQL (relational) databases, NoSQL (non-relational databases), or any combination (e.g., hybrid databases). For example, one or more of databases 111A-111D can comprise NoSQL databases such as column store databases, key-value store databases, document store databases, graph databases, multivalue databases, multimodel databases, or other NoSQL databases. In various embodiments, one or more of databases 111A-11D comprise analytic databases. Further, one or more of databases 111A-111D can comprise cloud-based databases, including cloud-based relational databases (such as, for example, Amazon Redshift, Amazon Aurora.MySQL, MariaDB, Oracle Database, or SQL Server) and cloud-based non-relational databases (such as, for example, SimpleDB, DynamoDB, MongoDB, or CosmosDB. The use of any combination of relational and non-relational, and cloud-based or locally-hosted databases, is within the scope of the present disclosure. Further, databases 111A-111D may run on data transmitting module 110, a dedicated computing device of DIP 108, another shared computing device of DIP 108, or any other computing device in electronic communication with DIP 108.

In various embodiments, data transmitting module 110 may request data from first user system 102 under predetermined circumstances. For example, data transmitting module 110 may request data from first user system 102 at predetermined intervals of time, such as every hour, every half hour, every 10 minutes, every 5 minutes, every 90 seconds, and/or every 1 minute. Further, data transmitting module 110 may request only data which has been entered or changed since a previous query. For example, data transmitting module 110 may be configured to request any new or changed data from first user system 102 every 90 seconds. Although described with reference to specific predetermined circumstances and time intervals, any manner of transmitting data from first user system 102 to data transmitting module 110 is within the scope of the present disclosure.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

In various embodiments, DIP 108 further comprises a data processing module 112 in communication with formatted database 111. Data processing module 112 may, for example, retrieve data from formatted database 111, perform operations on the data, and write to formatted database 111 newly created and/or processed data for storage and subsequent retrieval. Data processing module 112 may be an application running on data transmitting module 110, a dedicated computing device of DIP 108, another shared computing device of DIP 108, or any other computing device in electronic communication with DIP 108.

Data processing module 112 may comprise, for example, one or more software applications. In various embodiments, data processing module 112 comprises software applications configured to process data transmitted from first user system 102 and return relevant data to formatted database 111. For example, data processing module 112 can access formatted data transmitted by first user system 102 and stored within formatted database 111, and the software applications of data processing module 112 can manipulate and process the data to produce a number of data sets, including one or more sets of revenue data, schedule data, patient data, or other data. The newly-created data sets can be stored in formatted database 111. Data processing module 112 may thus generate models and analysis of individual dental practices as the practices relate to the models and thereby generate insight into the individual dental practices.

In various embodiments, DIP 108 further comprises an application server 113. Application server 113 may, for example, transmit data from data processing module to interfaces outside of DIP 108. For example, application server 113 can host web sites and provide backend support for web applications. In various embodiments, application server 113 is configured to transmit data, including newly-created data, from formatted database to one or more user interfaces.

With reference back to FIG. 1B, system 100B can comprise, for example, multiple application servers 113. In various embodiments, system 100B comprises one or more of a user interface application server, a consultant interface application server, a dashboard application server, an action center application server, or any combination of application servers, including multiple application servers of the same type.

In various embodiments, the dental practice utilizing first user system 102 can access, via a network (including the internet), a first user interface 115. For example, application server 113 can display data to first user system 102 through first user interface 115. Further, first user interface 115 can be used to transmit commands or requests to other components of system 100B, through, for example, application server 113.

Figure 2:
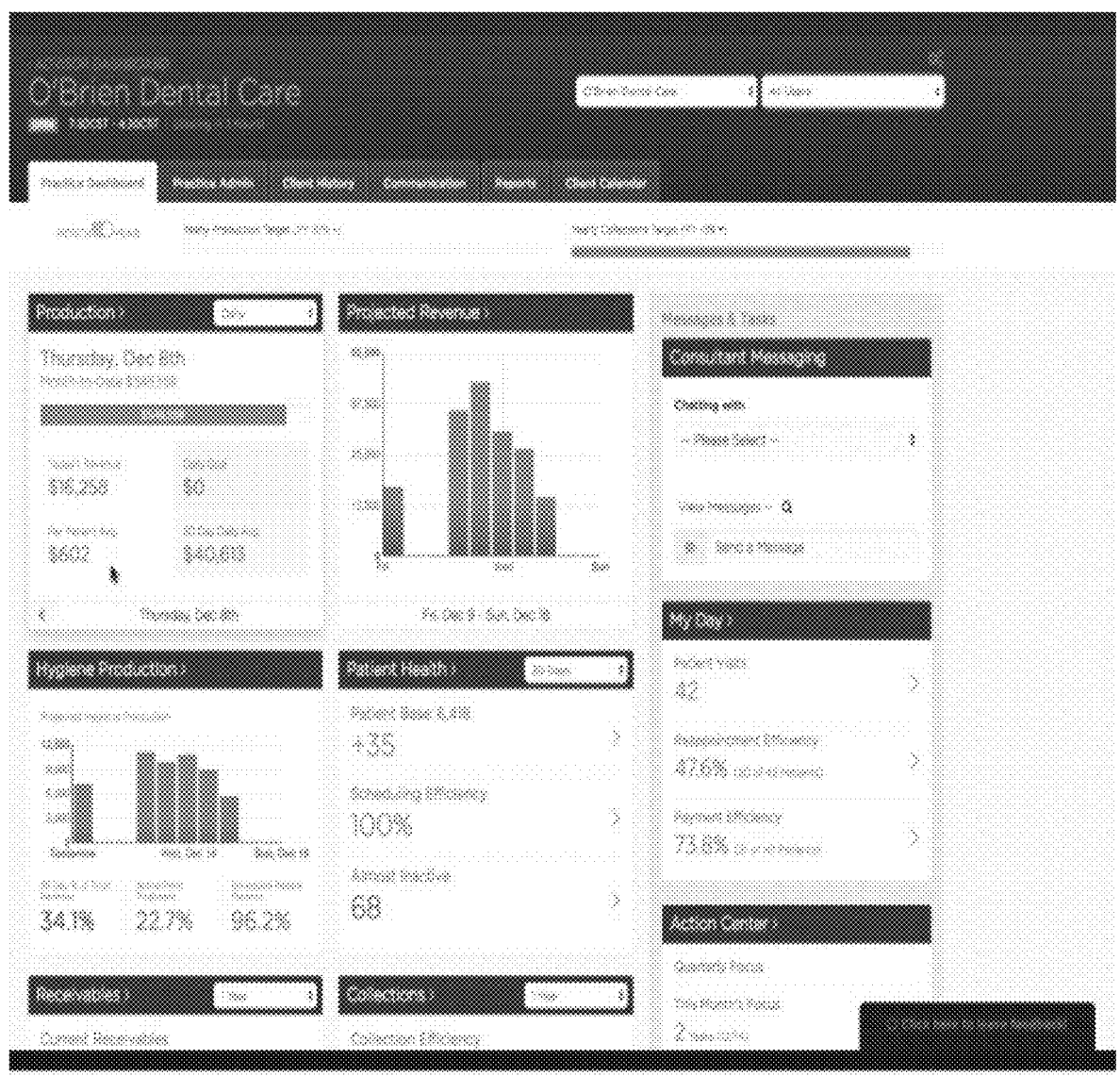
FIG. 2 illustrates a graphical user interface of a dashboard of a dental integration platform, in accordance with various embodiments.

In various embodiments, first user interface 115 comprises a graphical user interface. For example, with reference to FIG. 2, a first user interface 115 comprising a graphical user interface dashboard 200 is illustrated. In various embodiments, dashboard 200 provides visual representation of data that has been formatted, processed, created, and otherwise manipulated by DIP 108. Visual representations of data can comprise text, symbols, graphical representations, and any other representation that can be perceived visually. For example, one or more sets of revenue data, schedule data, patient data, or other data can be visually represented by first user system 102 and/or data transmitting module 110 to employees of the dental practice. Dashboard 200 may provide a landing screen for a dental practice, from which one may navigate to the various applications and interfaces described herein.

In various embodiments, first user interface 115 comprises a non-visual user interface. For example, first user interface 115 may comprise a voice user interface. Although further described with reference to specific embodiments (for example, graphical user interfaces) any type of interface is within the scope of the present disclosure.

Further, first user interface 115 can comprise a data interface. For example, first user interface 115 can comprise a machine-implemented module, such as a machine learning module, an artificial intelligence interface, an API, a file transfer protocol client, or any other programmable interface which allows for machine-to-machine communication.

With reference to FIG. 1A, system 100A may comprise a second user interface 116 and/or a third user interface 117. In various embodiments, each of first user interface 115, second user interface 116, and third user interface 117 is configured to display, convey, or otherwise communicate information relevant to their respective user systems (first user system 102, second user system 104, and third user system 106). Although described with reference to specific user systems and interfaces (first, second, and third user systems and interfaces), the use of any number of user systems and user interfaces is within the scope of the present disclosure.

Figure 1C:
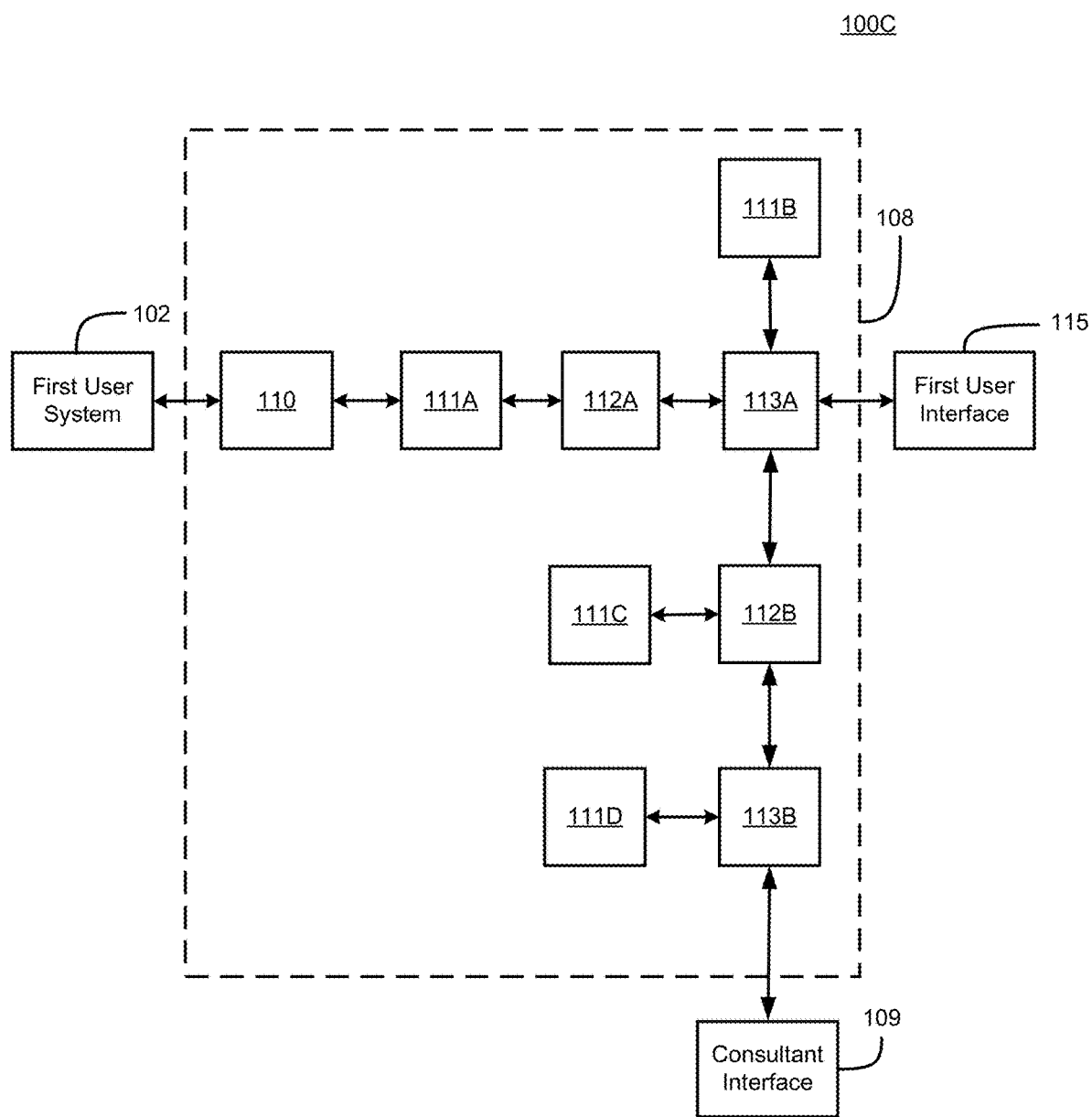
FIG. 1C illustrates yet another system for dental practice planning and management, in accordance with various embodiments.

With reference to FIG. 1C, a system 100C in accordance with various embodiments is illustrated. System 100C can comprise, for example, first user system 102. First user system 102 comprises a computer based system located in a dental office which utilizes a DPMS. In various embodiments, the DPMS comprises a database that is the system of record for data stored within first user system 102, e.g., data relating to the dental practice such as patient data, treatment data, financial data, and business operation data.

First user system 102 can, for example, communicate with data transmitting module 110 of system 100C. In various embodiments, first user system 102 can provide data transmitting module 110 with data in the native format of the DPMS, i.e., not formatted for system 100C. Data transmitting module 110 can convert data in the native format of the DPMS to data of the format utilized by the components of DIP 108. In that regard, fields from the database or data store of a DPMS may be mapped and migrated into a database or data store having a schema suitable to support DIP 108. One or more fields from the DPMS may be read and processed into a format suitable for DIP 108, The result of the processed data from the DPMS may then be written into DIP 108. In other embodiments, first user system 102 can comprise a conversion application which converts the data from the native format of the DPMS to the format anticipated and utilized by system 100C.

In various embodiments, system 100C further comprises system database 111A. System database 111A can, for example, be in communication with and capable of receiving data from data transmitting module 110A. In various embodiments, system database 111A can store data from multiple different user systems, in a common format.

System 100C can further comprise, for example, a logic data processing module 112A. For example, logic data processing module 112A can be in communication with system database 111A and perform logic operations on the data stored within systems database 111A.

In various embodiments, system 100C further comprises a dashboard application server 113A. For example, dashboard application server 113A can be in communication with logic data processing module 112A. Further, dashboard application server 113A can be in communication with first user interface 115. In such embodiments, dashboard application server 113A can transmit data for display on first user interface 115, and can receive commands, requests, and instructions from a user through first user interface 115.

Dashboard application server 113A can, for example, be in communication with a periodic trend database 111B. In various embodiments, periodic trend database 111B can receive and store data captured by system 100C from first user system 102 at various points in time, and store such data chronologically. For example, periodic trend database 111B may capture a set or subset of data at a specific point in time (e.g., a snapshot) at specific intervals of time.

System 100C can further comprise, for example, a key findings and opportunity report data processing module ("KFOR") 112B. KFOR 112B can, for example, be in communication with an issue database 111C. In various embodiments, KFOR 112B can be in communication with an action center application server 113B. Action center application server 113B can, for example, deliver content, receive commands and instructions, and be visually represented on the first user interface 115. Although described with reference to a particular type of data processing module (i.e., the KFOR) any type of data processing module can be utilized in connection with action center application server 113B.

Action center application server 113B can, for example, be in communication with a consultant interface 109. In various embodiments, action center application server 113B can transmit data to be displayed, conveyed, or otherwise communicated by consultant interface 109, and can receive commands, requests, and instructions from a user (e.g., a consultant) through consultant interface 109.

In various embodiments, consultant interface 109 can comprise a machine-to-machine interface. Similar to user interfaces 115, 116, and 117, consultant interface 109 can comprise a machine learning module, an artificial intelligence module, an API, a file transfer protocol client, or any other programmable machine-to-machine interface.

Figure 3:
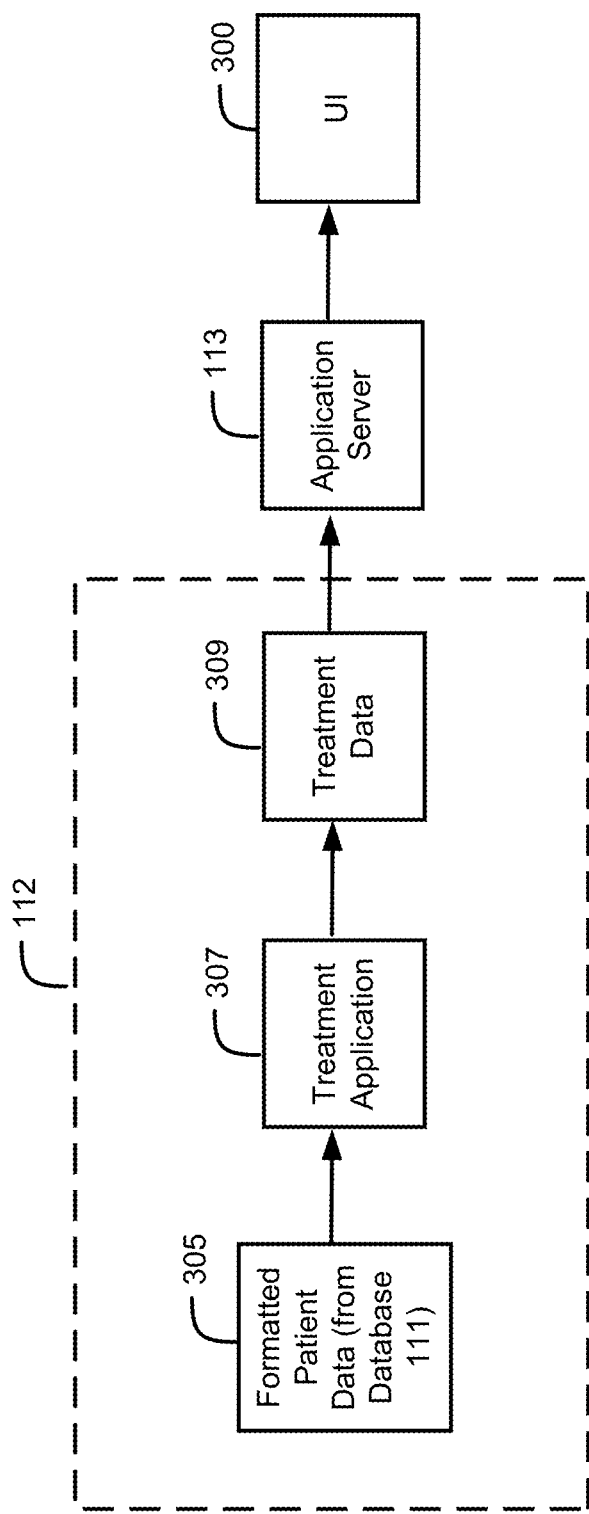
FIG. 3 illustrates a flow chart for the operation of a treatment application of the dental integration platform, in accordance with various embodiments.

With reference to FIG. 3, an exemplary software application (treatment application 307) running within data processing module 112 is illustrated. Treatment application may provide support for dashboard 200 of FIG. 2 and/or other interfaces by retrieving, analyzing, and providing data to populate the various fields and displays of the interfaces. For example, treatment application 307 can retrieve a set of formatted patient data 305 from formatted database 111 for processing. In various embodiments, formatted patient data 305 comprises information such as patient names, ages, sex, histories of treatments performed by the dental practice, histories of treatments performed by other dental practices, and other information relating to patients of the dental practice.

Treatment application 307 can, for example, process formatted patient data 305 for each patient of the dental practice, and create a set of treatment data 309. In various embodiments, treatment data 309 comprises a treatment plan for each patient of formatted patient data 305. Treatment plans can comprise one or more recommended treatments for a particular patient, including recommended dates for scheduling of the treatment. Treatment data 309 may further comprise projected financial data, such as projected revenue and/or projected expenses, based on the total number and types of treatments and/or treatment estimates contained in treatment data 309.

In various embodiments, treatment data 309 is stored within formatted database 111, where it can be stored and/or retrieved by application server 113. Application server 113 may, for example, prepare and format treatment data 309 for transmittal to first user interface 115.

With reference to FIG. 3, a UI 300 may, for example, visually represent and communicate various aspects of treatment data 309. For example, UI 300 may visually represent a planning efficiency of treatment data 309. In various embodiments, planning efficiency comprises a comparison of potential revenue generated by the treatment recommendations of treatment data 309 with other aspects of treatment data 309, including the total of treatments accepted and/or scheduled, and the total of treatments completed and/or performed by the dental practice. The information presented may indicate the importance of effective scheduling and follow up.

In various embodiments, UI 300 can represents (for example, visually) a projected revenue corresponding to treatment data 309. The projected revenue may, for example, comprise an estimate of revenue that will be collected in a specified time frame based on, in part, the total of treatments accepted and/or scheduled and the total of treatments completed and/or performed by the dental practice. As described in connection with user interfaces 115, 116, and 117, UI 300 can comprise a non-visual interface, such as a voice interface, and/or a machine-to-machine interface, among other interfaces.

Although described with reference to specific data types (for example, planning efficiency, projected revenue, and procedure profiler), treatment data 309 can comprise any data calculated or created from, at least in part, formatted patient data 305. Further, UI 300 can demonstrate (for example, visually) any or all aspects of treatment data 309, including only those aspects of treatment data 309 predetermined and/or selected by the dental practice. Further, UI 300 may, for example, be configured to visually represent different aspects of treatment data 309 based on a particular user (e.g., a specific employee of the dental practice).

Figure 4:
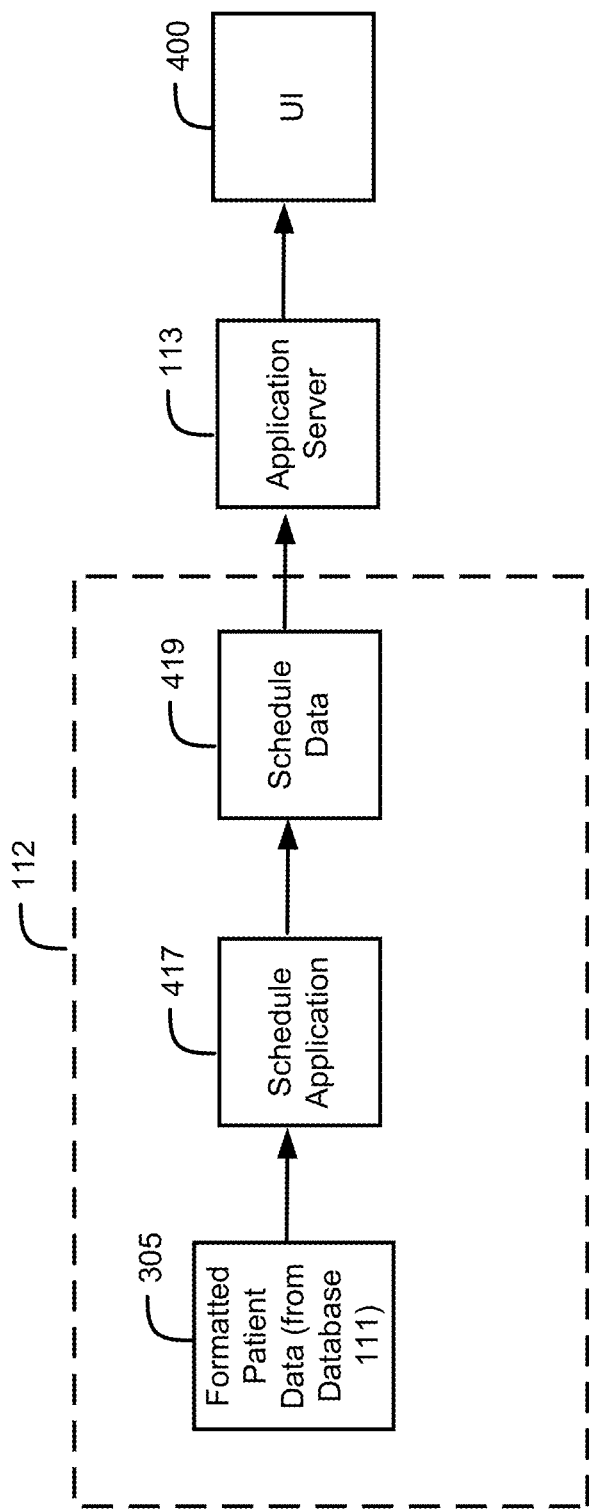
FIG. 4 illustrates a flow chart for the operation of a software application of the dental integration platform for managing day-to-day operations, in accordance with various embodiments.

With reference to FIG. 4, another exemplary software application (schedule application 417) running within data processing module 112 is illustrated. For example, schedule application 417 can receive formatted patient data 305 from formatted database 111 for processing. As previously described, formatted patient data 305 may comprise, for example, information such as patient names, ages, sex, histories of treatments and procedures performed by the dental practice, histories of treatments performed by other dental practices, currently-scheduled treatments, and other information relating to patients of the dental practice.

Schedule application 417 may, for example, process formatted patient data 305 for each patient of the dental practice, and create a set of schedule data 419. In various embodiments, schedule data 419 comprises a daily schedule which includes each treatment planned for each patient on a specified day. Daily schedules of schedule data 419 may comprise one or of an individual schedule, wherein the individual schedule includes each and every treatment assigned and/or scheduled to be performed by a particular user (e.g., employee of the dental practice). Stated another way, schedule data 419 may comprise a daily schedule of treatments to be performed by each employee of the dental practice. Schedule data 419 may be accompanied by suggestions for improvement in practice management and/or practical skills based on comparison of the subject dental practice with peers at peer dental practices.

In various embodiments, formatted patient data 305 transmitted to schedule application 417 can comprise data from a plurality of user systems, including first user system 102, second user system 104, and/or third user system 106. Schedule application 417 may, for example, generate one or more schedule models (within schedule data 419) from formatted patient data 305. In various embodiments, the schedule models of schedule data 419 comprise one or more of an average time period from planned to accepted ($T_{PA}$), an average time period from accepted to scheduled ($T_{AS}$), an average time period from scheduled to completed ($T_{SC}$), and an average time period from planned to completed ($T_{PC}$) of the various applicable dental practices, wherein the averages are taken across the plurality of user systems.

Multiple schedule models may be generated for the purposes of comparing a single dental practice (such as, for example, the dental practice utilizing first user system 102) to a plurality of other dental practices (such as, for example, the dental practices using second user system 104 and third user system 106). In various embodiments, the individual dental practices included in the plurality of dental practices are selected based on one or more predetermined characteristics. For example, one or more schedule models can be generated by processing the patient data of dental practices sharing one or more characteristics with an individual dental practice, including number of patients, geographical market, number of service providers, number of employees, age of operation of practice, and other relevant characteristics. In that regard, dental practices may be categorized based on characteristics (e.g., demographics) of dental practices and compared to dental practices within the same or similar demographic groups.

After one or more schedule models are generated, schedule application 417 can compare the models to schedule data 419 of first user system 102, and generate a set of schedule comparison data. One or more aspects of the set of schedule comparison data may, for example, be transmitted or visually represented to a UI 400 and/or first user interface 115.

In various embodiments, schedule data 419 is transmitted to formatted database 111, where it can be retrieved by data transmitting module 110 and/or application server 113. Application server 113 may, for example, prepare and format schedule data 419 for transmittal to UI 400 and/or first user interface 115.

Figure 6:
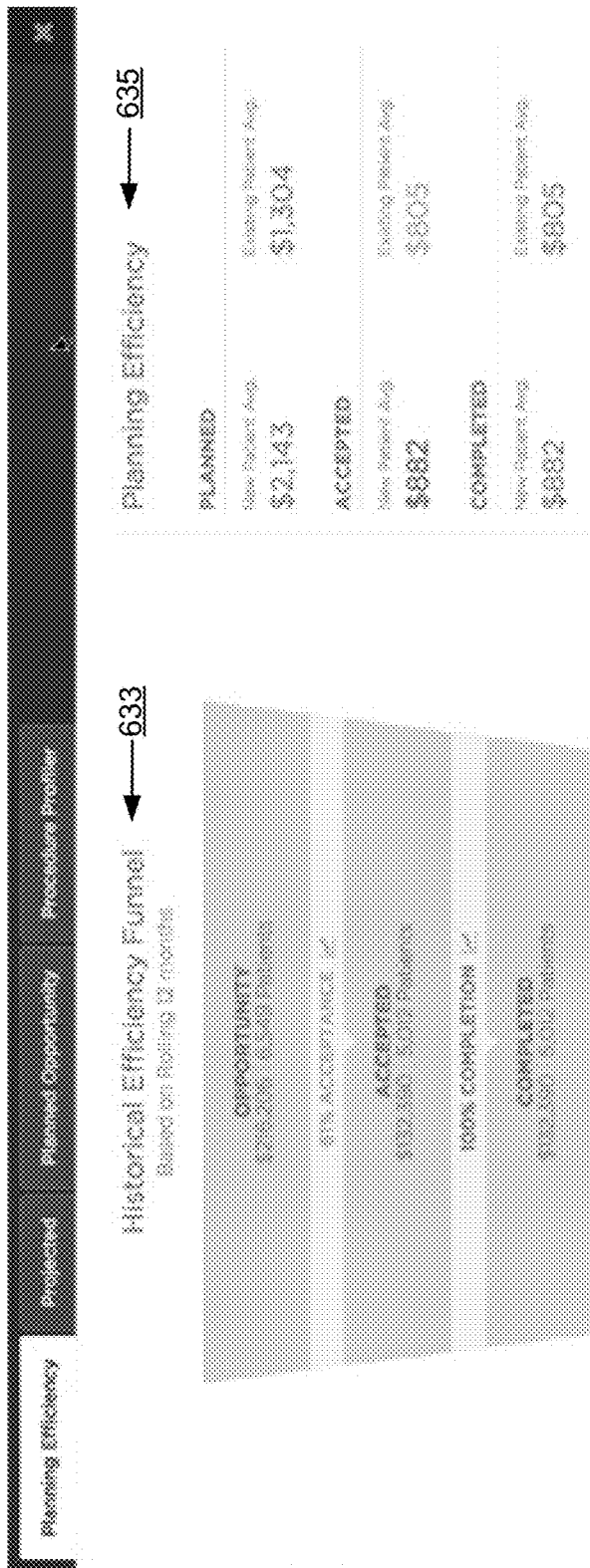
FIG. 6 illustrates another graphical user interface of the software application of FIG. 4, in accordance with various embodiments.

With reference to FIGS. 5 and 6, a UI 500A and UI 500B may represent (for example, visually) various aspects of schedule data 419. For example, UI 500A may visually represent a daily schedule 521 of schedule data 419. In various embodiments, daily schedule 521 comprises a list of all treatments scheduled for a specified day, as well as the patient corresponding to each treatment, and the provider (e.g., employee of the dental practice) assigned to carry out the treatment.

For example, UI 500B may visually represent an historical efficiency funnel 633, and/or a planning efficiency 635. In various embodiments, each of historical efficiency funnel 633 and/or planning efficiency 635 are created from analysis of formatted patient data 111 and/or schedule data 419, and can be displayed, conveyed, or otherwise communicated to one or more users, such as employees of the dental practice.

Although described with reference to particular aspects of schedule data 419, UI 500A and/or UI 500B can be configured to represent any aspect of schedule data 419 based on a particular user (e.g., an employee of the dental practice), as well as any other criteria.

In various embodiments, system 100 comprises a plurality of user systems. Each user system, such as second user system 104 and third user system 106, transmits data to and from the same DIP 108. In various embodiments, first user system 102, second user system 104, and/or third user system 106 utilize different data formats, software, and/or hardware from each other. In such embodiments, data transmitting module 110 can be configured to receive data in different formats from one or more user systems 102, 104, and 106, and convert and/or format the data to a common format for storage within database 111.

In various embodiments having more than a single user system (e.g., first user system 102), DIP 108 can comprise more than one data transmitting module 110 and/or more than one formatted database 111. Although illustrated with reference to a single data transmitting module 110 and a single formatted database 111 (as well as three user systems), one having skill in the art will appreciate that a larger number of user systems may scale into the system by incorporating additional data transmitting modules 110 and/or databases 111.

User systems (such as 102, 104, and/or 106) can transmit to DIP 108 identifiable characteristics of the dental practice utilizing each of the user systems. For example, first user system 102, second user system 104, and/or third user system 106 can each transmit to DIP 108 various characteristics of their respective dental practices, including number of patients, geographical market, number of service providers, number of employees, age of operation of practice, and other relevant characteristics. As will be described in further detail, the identifiable characteristics of the dental practice utilizing each of the user systems may be used to compare dental practices having similar characteristics in a quantitative manner.

Figure 7:
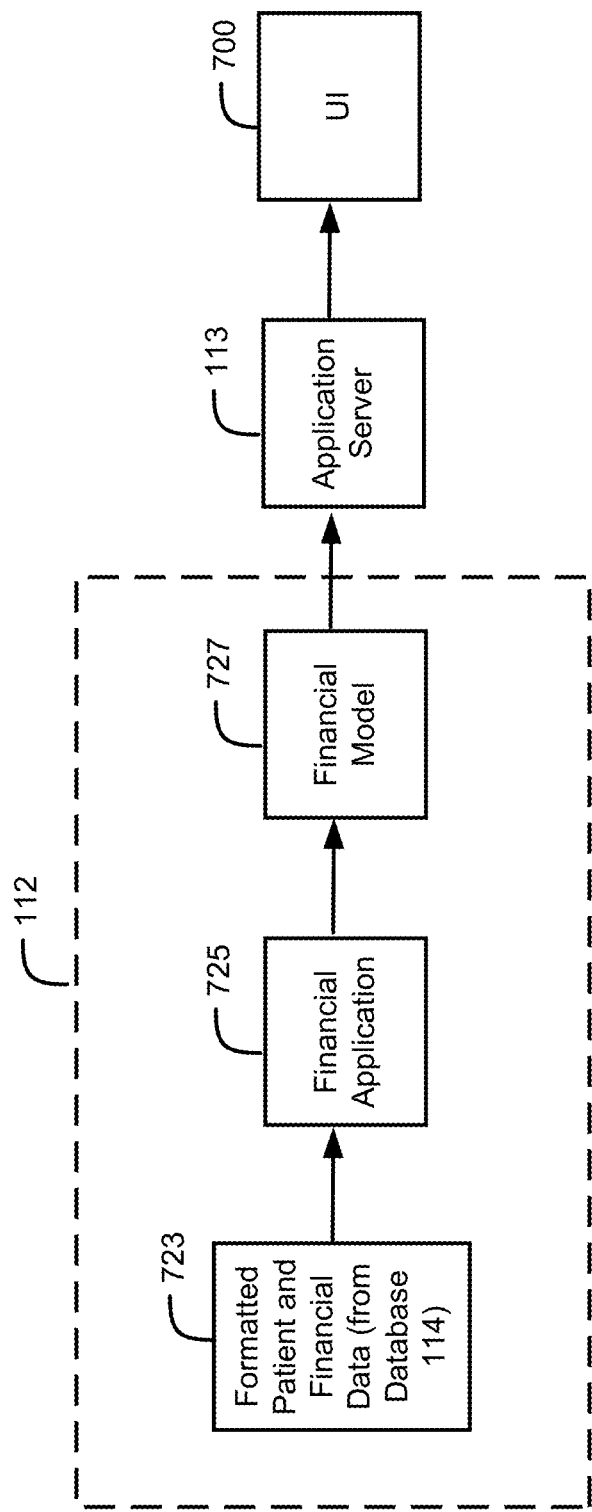
FIG. 7 illustrates a flow chart for the operation of a software application of the dental integration platform for monitoring and analysis of accounts receivables and collections, in accordance with various embodiments.

With reference to FIG. 7, yet another exemplary software application (financial application 725) running within data processing module 112 is illustrated. For example, financial application 725 can receive formatted patient and financial data 723 from formatted database 111 for processing. Formatted patient and financial data 723 can comprise, in part, formatted patient data 305 (of FIGS. 3 and 5), as well as formatted financial data (e.g., revenue and/or expense data) of the dental practice.

In various embodiments, similarly to schedule application 417, financial application 725 may generate financial projections based on formatted patient and financial data 723. For example, financial application 725 may generate one or more parameters or factors that may then be used to generate financial projections for the dental practice. For example, the factors or parameters generated by financial application 725 may include one or more of a potential revenue of planned to accepted ($R_{PA}$), a percentage revenue of planned to accepted (% $R_{PA}$), a potential revenue of accepted to scheduled ($R_{AS}$), a potential revenue of scheduled to completed ($R_{SC}$), and a percentage revenue of accepted to completed (% $R_{AC}$). These factors may, for example, be generated using formatted patient and financial data 723 corresponding to year-to-date data (e.g., data generated from the first day of the present year to the present date on which the financial application 725 is generating the factors).

After generating one or more factors, financial application 725 can utilize the factors to calculate projected financials. For example, financial application 725 can generate projected revenues and/or expenses for a predetermined time frame, such as a quarter, a year, or any desired period, or financial application 725 can generate projected revenues and/or expenses for selected time frames based on a start and stop date input by a user of first user system 102. For example, financial application 725 can generate one or more of a projected treatment revenue, a projected accepted revenue, a projected completed revenue, and/or various expense data for any predetermined time period.

In various embodiments, formatted patient and financial data 723 can comprise data from a plurality of user systems, including first user system 102, second user system 104, and/or third user system 106. Financial application 725 may, for example, generate one or more financial models 727 from formatted patient and financial data 723. In various embodiments, financial models 727 comprises one or more of an average annual potential revenue, an average annual accepted revenue, an average completed revenue, various expense data, an average $T_{PA}$, an average $T_{AS}$, an average $T_{SC}$, and an average $T_{PC}$ of the various applicable dental practices, wherein the average is taken across the plurality of user systems.

Multiple financial models may be generated for the purposes of comparing a single dental practice (such as, for example, the dental practice utilizing first user system 102) to a plurality of other dental practices. In various embodiments, each of the dental practices of the plurality of dental practices are selected based on a predetermined characteristic. For example, one or more financial models can be generated by processing the patient and financial data of dental practices sharing one or more characteristics with an individual dental practice, including number of patients, geographical market, number of service providers, number of employees, age of operation of practice, and other relevant characteristics.

After one or more financial models are generated, financial application 725 can compare the models to financial model 727 of first user system 102, and generate a set of financial comparison data. One or more aspects of the set of financial comparison data may, for example, be transmitted or visually represented to first user interface 115.

In various embodiments, financial model 727 is transmitted to formatted database 111, where it can be retrieved by data transmitting module 110 and/or application server 113. Application server 113 may, for example, prepare and format financial model 727 for transmittal to first user interface 115.

Figure 8:
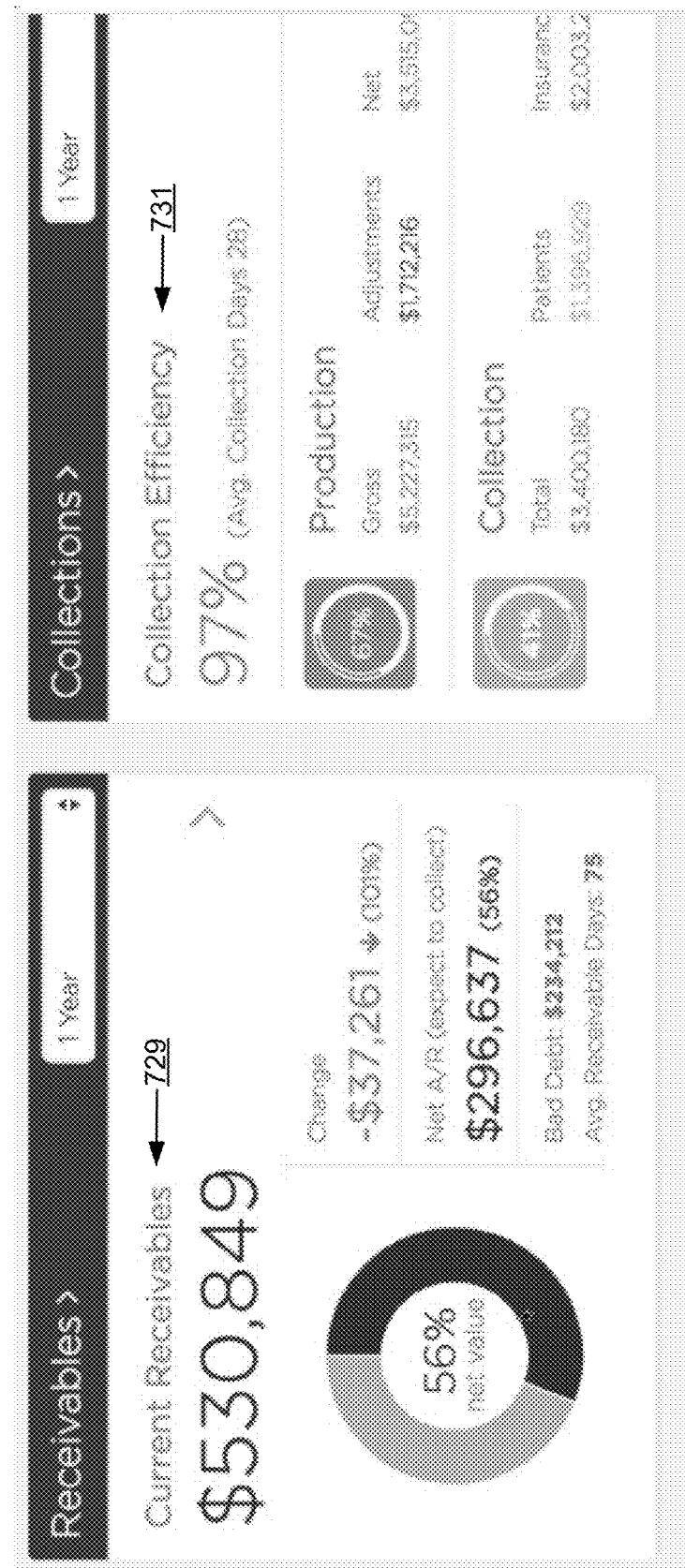
FIG. 8 illustrates a graphical user interface of the software application of FIG. 7, in accordance with various embodiments.

With reference to FIGS. 7 and 8, a UI 700 may, for example, visually represent and communicate various aspects of financial model 727. For example, UI 700 may visually represent a current receivables category 729 of financial model 727. Current receivables category 729 may comprise, for example, one or more revenue projections, including projections based on financial model 727 generated by financial application 725.

In various embodiments, UI 700 visually represents a collection efficiency category 731 of financial model 727. Collection efficiency category 731 may, for example, comprise total revenue collected for a predetermined time frame, total adjustments to billings made to patients for a predetermined time frame, total outstanding billings made to patients for a predetermined time frame, and any other collection-related data of financial model 727.

Although described with reference to specific data types (current receivables category 729 and collection efficiency category 731), financial model 727 can comprise any data calculated or created from, at least in part, patient and financial data 723. Further, UI 700 can visually demonstrate any or all aspects of financial model 727, including only those aspects of financial model 727 predetermined and/or selected by the dental practice. Further, UI 700 may, for example, be configured to visually represent different aspects of financial model 727 based on a particular user (e.g., an employee of the dental practice).

With reference to FIG. 1, system 100 can further comprise one or more consultant user interfaces 109. In various embodiments, consultant user interface 109 is in communication with DIP 108. Consultant user interface 109 may, for example, access data processing module 112 and/or formatted database 111. As previously noted, consultant user interface 109 can comprise a human operated interface (such as a GUI or other UI), or a machine-to-machine interface, such as a machine learning module, an artificial intelligence interface, an API, a file transfer protocol client, or any other programmable interface which allows for machine-to-machine communication.

In various embodiments, consultant user interface 109 may access data transmitted from a number of user systems, including first user system 102, second user system 104, and/or third user system 106, and to first user interface 115, second user interface 116, and/or third user interface 117. For example, consultant user interface 109 may access data, including treatment data (e.g., treatment data 309), schedule data (e.g., schedule data 419), and/or revenue data (e.g., financial model 727) for one or more user systems. In various embodiments, consultant user interface 109 can be utilized by a user (i.e., a consultant) capable of reviewing various data of dental practices and making recommendations for improvement. For example, a consultant utilizing consultant user interface 109 to analyze the data of first user system 102 may qualitatively analyze one or more of treatment data, schedule data, and revenue data to provide recommendations for improving one or more aspects of the performance of the dental practice.

In various embodiments, a user utilizing consultant user interface 109 may determine which aspects of treatment data, schedule data, revenue data, or other relevant data generated by DIP 108, is transmitted to one or more user interfaces. For example, consultant user interface 109 may direct data transmitting module 110 to transmit and/or visually represent data to first user interface 115, including a schedule model of schedule data 419 and/or financial model 727.

In other embodiments, consultant user interface 109 comprises a machine-to-machine interface which determines which data (such as treatment data, schedule data, and/or financial data) is transmitted to various components of system 100.

Figure 9:
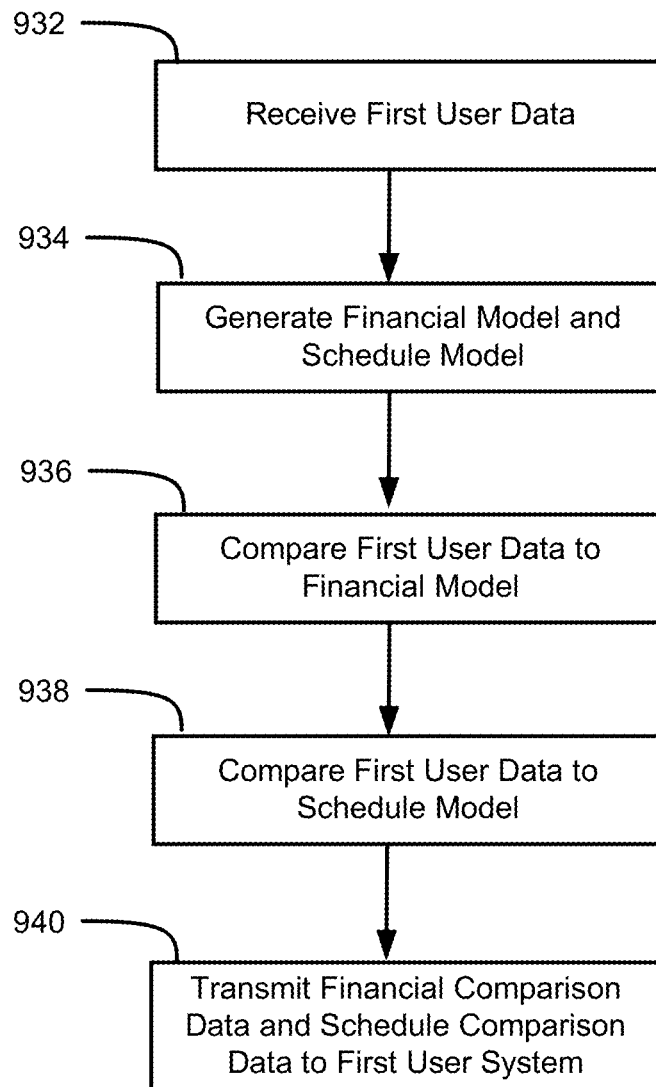
FIG. 9 illustrates a method for operating a dental integration platform in accordance with various embodiments.

With reference to FIGS. 1 and 9, a method 900 for operating a DIP (such as DIP 108) in accordance with various embodiments is illustrated. For example, method 900 may comprise a receive and format first user data step 932. In various embodiments, step 932 comprises first user system 102 transmitting data relevant to the operation of the dental practice to DIP 108, and the data is then formatted, stored, and processed by DIP 108.

In various embodiments, method 900 further comprises a generate financial model and schedule model step 934. For example, step 934 may comprise a data processing module (such as data processing module 112) generating one or more financial models and schedule modules from data provided by first user system 102., e.g., based on data provided by multiple other dental practices.

Method 900 may further comprise, for example, a compare first user data to financial model step 936. In various embodiments, step 936 may comprise a data processing module (such as data processing module 112) comparing data provided by first user system 102 to one or more financial models generated by step 934.

In various embodiments, method 900 further comprises a compare first user data to schedule model step 938. For example, step 938 may comprise a data processing module (such as data processing module 112) comparing data provided by first user system 102 to one or more schedule models generated by step 934.

Method 900 may further comprise, for example, a transmit financial comparison data and schedule comparison data to first user system step 940. In various embodiments, step 940 comprises transmitting comparison data created in steps 936 and 938 to first user interface 115.

Figure 10:
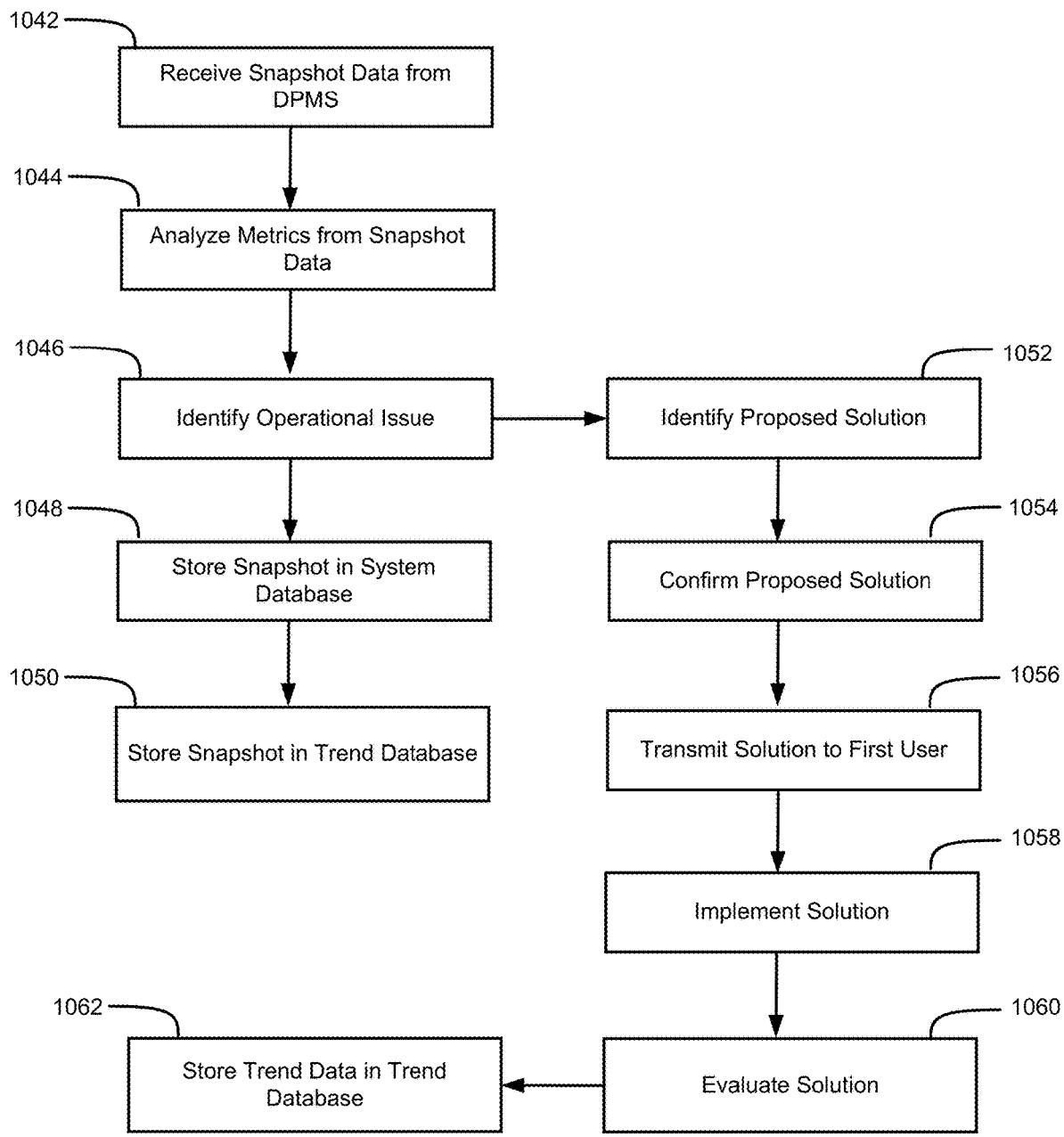
FIG. 10 illustrates a method for improving operations of a dental practice in accordance with various embodiments.

With reference to FIGS. 1C and 10, a method 1000 for improving operations of a dental practice in accordance with various embodiments is illustrated. For example, method 1000 can utilize systems 100A, 100B, and/or 100C of FIGS. 1A-1C to identify issues with the operation of a dental practice.

In various embodiments, method 1000 comprises a step 1042 of receiving snapshot data from a DPMS. For example, DIP 108 can receive from first user system 102 a data set the DPMS that is captured at a particular point in time (e.g., a snapshot). The data can comprise any relevant data from the operation of the dental practice that is stored within the DPMS, including, for example, any of patient data, treatment plans, schedule data, financial data (including revenue and/or expenses), treatment data (including total of treatments accepted and/or scheduled, and the total of treatments completed and/or performed by the dental practice), treatment planning, accepting, and completion rates, potential revenue of planned to accepted ($R_{PA}$), a percentage revenue of accepted to scheduled (% $R_{AS}$), a potential revenue of scheduled to completed ($R_{SC}$), and a percentage revenue of planned to completed (% $R_{PC}$). The snapshot data can be transmitted by data transmitting module 110 to system database 111A.

Method 1000 can further comprise, for example, a step 1044 of analyzing metrics from the snapshot data. In various embodiments, specific elements of the snapshot data can be compared to data stored within system database 111A. For example, system database 111A can comprise data models, against which elements of the snapshot data can be compared. With reference back to FIG. 9, system database 111A can comprise one or more of a financial model and a schedule model, as generated in step 934 of method 900. Although described with reference to specific models, step 1044 can comprise comparing any element of the snapshot data with any reference or reference value within system database 111A, including models generated by DIP 108.

Step 1044 can further comprise identifying, through analysis by, for example, logic data processing module 112A, one or more metrics, elements, or aspects of the dental practice of the first user that are a predetermined magnitude or amount less than a threshold or predicted value. For example, one or more metrics of the dental practice, such as an actual revenue, may be significantly less than a projected revenue for the dental practice. Step 1044 can comprise noting any and all metrics, elements, or aspects of the snapshot data that are a predetermined magnitude less than anticipated values.

In various embodiments, metrics of the snapshot data can be compared to corresponding goal metrics stored within, for example, system database 111A. In such embodiments, goal metrics can comprise an aspirational, expected, anticipated, calculated, or otherwise projected value for a specific metric over a desired time frame. For example, a goal metric can comprise a goal percentage revenue of planned to completed (% $R_{PC}$) over a specified time frame, such as 30 days, 60 days, 90 days, or any other suitable time interval. The metric of snapshot data (% $R_{PC}$) is compared to the goal metric % $R_{PC}$ over a specified time interval. If the metric % $R_{PC}$ of the snapshot data is a specified value or magnitude less than the goal metric % $R_{PC}$, the metric can be flagged for use in determining potential operation issues of the practice. Although illustrated with respect to a specific metric (% $R_{PC}$), step 1044 can comprise analyzing a multitude of metrics of the snapshot data. Goal metrics, for example, can be calculated and/or determined based on characteristics of the practice. For example, one or more goal metrics can be generated by processing the data of dental practices sharing one or more characteristics with an individual dental practice, including number of patients, geographical market, number of service providers, number of employees, age of operation of practice, and other relevant characteristics. In that regard, dental practices may be categorized based on characteristics (e.g., demographics) of dental practices and compared to dental practices within the same or similar demographic groups. In other words, goal metrics for a particular practice can be calculated from the performance and health (i.e., financial success) of other similar practices.

Further, goal metrics can be calculated or determined based on the performance and health (i.e., financial success) of non-similar practices. For example, particular metrics (for example, return on investment, profit margin ratio, and/or return on sales) can be determined and stored by the system independently of characteristics of the individual practice. Stated another way, goal metrics may comprise "standard" metrics that used to evaluate the performance and health of most or all dental practices. Although described with reference to specific methods of calculating goal metrics, the use of any type of goal metric, for any specified time interval, is within the scope of the present disclosure.

Figure 11:
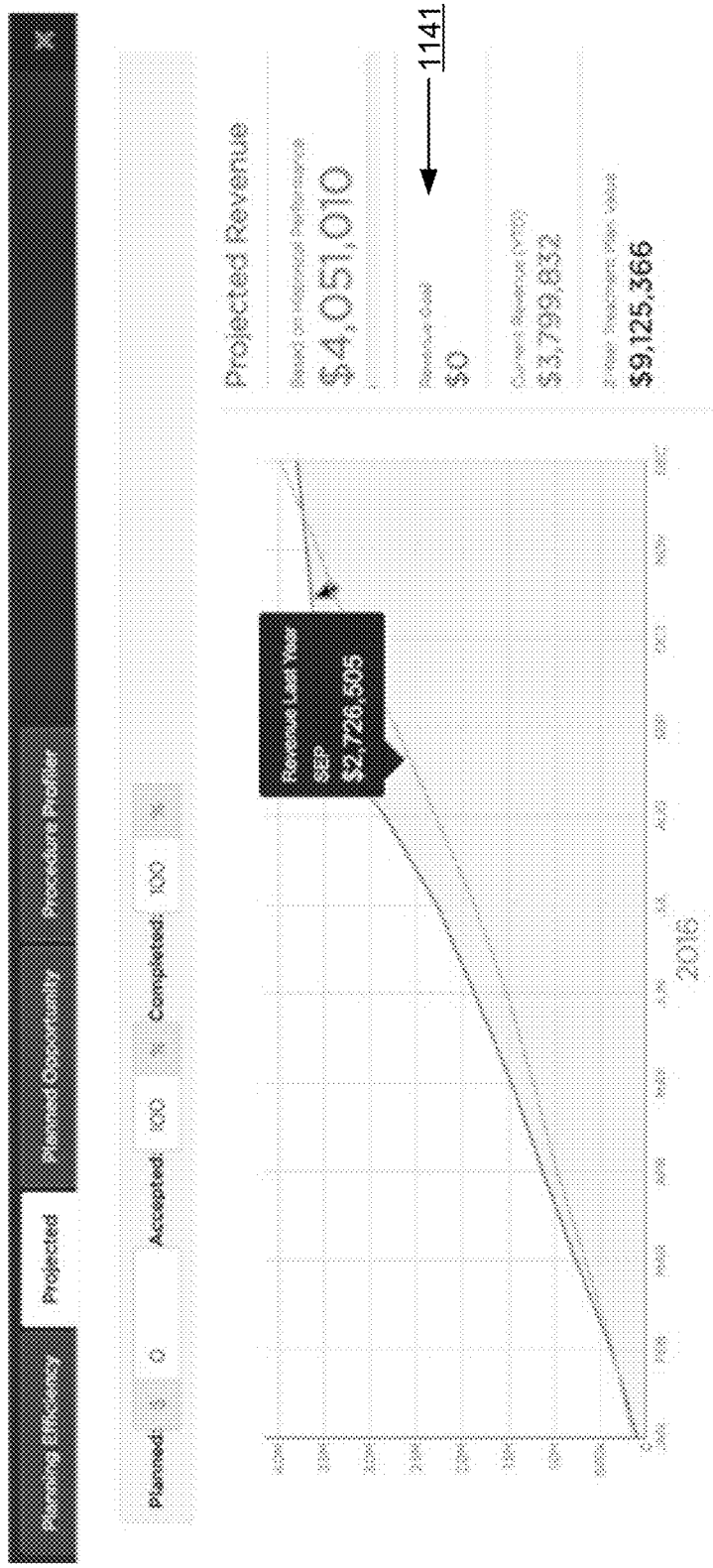
FIG. 11 illustrates a graphical display of a user interface in accordance with various embodiments.

With reference to FIG. 11, a UI 1100 illustrates a revenue goal 1141. In various embodiments, revenue goal 1141 is stored, for example, within system database 111A. For example, step 1044 can comprise comparing or more metrics of the snapshot data to revenue goal 1141. Further, UI 1100 can display, convey, or otherwise communicate information regarding revenue goal 1141 and any related metrics or numerical values, such as a projected revenue, a current year-to-date revenue, a projected treatment plan revenue, or any other related numerical value.

Figure 12:
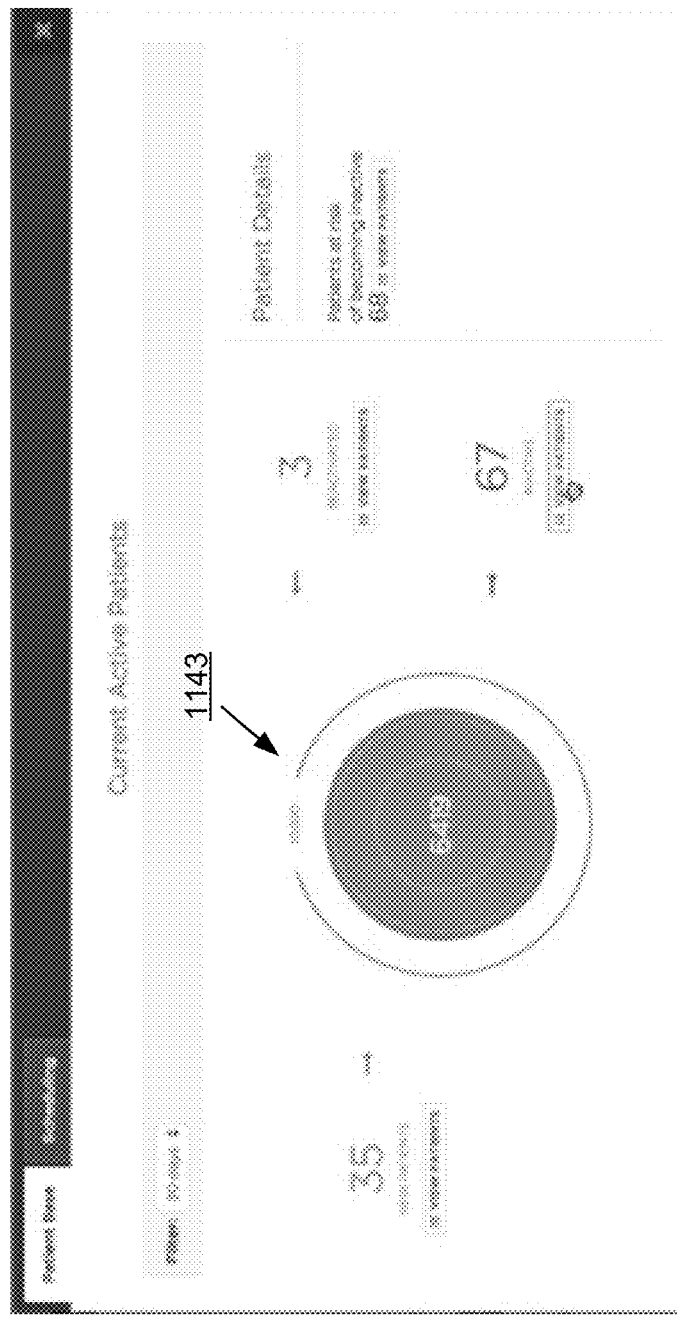
FIG. 12 illustrates another graphical display of a user interface in accordance with various embodiments.

With reference to FIG. 12, a UI 1200 illustrates a patient base goal 1143. For example, patient base goal 1143 can comprise a goal of the total number of patients of a dental practice determined, at least partially, by examining the patient base of a plurality of other dental practices sharing one or more characteristics or demographics with the dental practice utilizing systems 100A-100C. Step 1044 can comprise comparing one or more metrics of the snapshot data (such as the total number of patients of the dental practice) to patient base goal 1143. Further, UI 1200 can display, convey, or otherwise communicate information regarding patient base goal 1143 and any related metrics or numerical values, such as a number of new patient, a number of reactivated patients, a number of inactive patients, a number of patients at risk of becoming inactive, or any other related numerical value.

In various embodiments, method 1000 further comprises a step 1046 of identifying an operational issue. For example, step 1046 can comprising transmitting one or more metrics of the snapshot data that are below their respective anticipated, goal, and/or threshold values. In such embodiments, step 1046 can comprise utilizing KFOR 112B to identify an operational issue by comparing the metrics determined in step 1044 with one or more issue profiles stored, for example, within issue database 111C. In various embodiments, KFOR 112B can produce a report identifying and describing the operational issues, such as, for example, a key findings and opportunity report. Although described with reference to a particular type of data processing module (i.e., the KFOR) any type of data processing module can be utilized to identify an operation issue.

In various embodiments, an issue profile can comprise a list of metrics which deviate from their respective anticipated, goal, and/or threshold values, and a particular issue which the deviations implicate. For example, step 1044 can determine that a hygiene retention rate is 70% and the projected revenue is 4% below the corresponding goal metric, and transmit these metrics to KFOR 112B. KFOR 112B can compare these metrics with the issue profiles in issue database 111C, and determine that these two metrics are associated with an issue profile that denotes a failure to retain patients for dental hygiene procedures. Further, this issue may be indicated on the key findings and opportunity report.

If no operational issues are identified in step 1046, method 1000 can comprise a step 1048 of storing the snapshot data in system data base 1048. For example, the snapshot data received in step 1042 can be stored within the system database 111A of DIP 108. As previously described, the snapshot data may be combined with the data of other dental practices, sharing one or more elements of demographic data, to create and/or improve models stored within and used by DIP 108. Further, method 1000 can comprise a step 1050 of storing the snapshot data in trend database 111B.

In various embodiments, method 1000 further comprises a step 1052 of identifying a proposed solution. For example, for each of the issues identified in step 1046, DIP 108 can determine one or more proposed solutions to each issue. Step 1052 can comprise identifying a potential change or series of changes to be undertaken by the dental practice to address the issue identified in step 1046. Further, step 1052 can comprise comparing the issue(s) identified in step 1046 with, for example, content stored within content database 111D, and creating one or more proposed solutions to address the issues.

Method 1000 can further comprise, for example, a step 1054 of confirming the proposed solutions. For example, step 1054 can comprise transmitting the proposed solutions to a consultant interface 109, where the proposed solutions are evaluated by a consultant. Any data or information relevant to the proposed solutions may also be displayed, conveyed, or otherwise communicated to the consultant. For example, the indicators transmitted in step 1044, the issue profile, and the proposed solution can be communicated to the consultant. In various embodiments, the consultant can review and confirm each of the proposed solutions from step 1054.

In other embodiments, step 1054 comprises confirming the proposed solution via a machine-to-machine interface 109. For example, step 1054 can comprise confirming, by a machine learning interface, an artificial intelligence interface, or any other suitable machine-to-machine interface capable of automatically confirming the proposed solution without input from the consultant.

In various embodiments, method 1000 can comprise a step 1056 of transmitting the confirmed solution to the first user. For example, each of the solutions confirmed in step 1054 are transmitted, for example, to the first user interface 115. In various embodiments, the solutions are displayed, conveyed, or otherwise communicated to first user interface 115 by the action center application server 113B. Step 1056 comprises providing any aspect of the confirmed solution, including links to content (such as content stored within content database 111D) and instructions, necessary for the first user to implement the solution in the dental practice and the DPMS of the first user system 102.

Method 1000 further comprises, for example, a step 1058 of implementing the solutions. In various embodiments, step 1058 comprises the first user reviewing the content (such as content stored within content database 111D) and instructions provided by step 1056, and subsequently implementing any recommended changes. For example, if (as previously described) the dental practice is experiencing the issue of "failure to retain patients for dental hygiene procedures," step 1058 may indicate to the first user that employees (such as the dental hygienists and/or schedulers) should undertake training to improve their ability to "sell" hygiene procedures. Such training content is provided to the first user via the content database 111D and the first user interface 115.

In other embodiments, step 1058 comprises implementing the proposed solution by, for example, a machine learning module, an artificial intelligence module, or any other automatic and computer implemented module, program, subroutine, or interface. In such embodiments, the proposed solution is not evaluated by a human (such as first user). Instead, the proposed solution is evaluated by the computer implemented module, program, subroutine, or interface, and if the solution meets a set of predetermined criteria, the solution is implemented. The predetermined criteria can comprise any suitable measure of the potential effectiveness of the proposed solution, including, among others, the historical effectiveness of the solution in other practices including practices sharing one or more characteristics or demographics with the individual practice.

In various embodiments, method 1000 further comprises a step 1060 of evaluating the solution. Step 1060 can comprise, for example, obtaining further snapshot data (i.e., "trend data") from the first user system 102 at specific time periods after the implementation of the solution (such as, for example, step 1058). For example, trend data can be received by DIP 108 at periods of 30, 60, 90, and 120 days or longer after implementation of the solution. Although described with reference to specific time periods, any frequency of obtaining trend data is within the scope of the present disclosure. The trend data may be, for example, a series of data points that include metric values and/or an indicators at a corresponding time and/or date. In that regard, trend data may be represented as a set of tuples (e.g., [60%, Jan. 1, 2017], [68%, Jan. 15, 2017], [79%, Feb. 1, 2017], [83%, Mar. 1, 2017]). The trend data may thus be illustrative of changes in performance metrics over time suitable for analysis to identify whether a solution had a positive, negative, or negligible impact on the metrics.

Trend data can be compared for example, by logic data processing module 112A, to expected change and/or improvement in the metric or metrics to which the solution is directed. In various embodiments, an expected change and/or improvement can include both a magnitude of change or improvement as well as a corresponding time interval. For example, in the scenario described previously (the issue of a failure to retain patients for dental hygiene procedures), a solution can be associated with an expected improvement of the hygiene retention rate from 70% (as measured in the snapshot data) to 75%, and the projected revenue from 4% less than the goal metric to meeting the goal metric (i.e., zero % less than the goal metric) with 90 days. Step 1058 can comprise evaluating the trend data at 90 days after implementation of the solution, and comparing the hygiene retention rate and projected revenue of the trend data to the expected values of the solution. If the hygiene retention rate and/or projected revenue are at higher than the expected values of the solution, the solution is determined to be successfully. An unsuccessful solution would result in either no change or an increase in the indicators identified during step 1044.

Step 1060 can further comprise modifying issue database 111C to reflect the success or failure of the implemented solutions. In various embodiments, if a solution is determined to be successful, step 1060 can modify the issue profile of the specific issue to reflect additional success, specifically, success in the dental practice of the first user. If a solution is determined to be unsuccessful, the issue profile of the specific issue may be modified to reflect the lack of success of the implemented solution, and, potentially, to not propose the solution for addressing the specific issue in the future.

In various embodiments, step 1060 comprises evaluation of the implemented solution by, for example, a machine learning module and/or an artificial intelligence module. If a particular implemented solution is determined to be unsuccessful after a predetermined number of implementations (across one or more dental practices), the machine learning module and/or artificial module may discontinue or remove the solution from the pool of potential solutions. Conversely, if a particular implemented solution is successful after a predetermined number of implementations, the machine learning module and/or artificial intelligence module can prioritize the solution over other potential solutions for the same issue. In such embodiments, the machine learning module and/or the artificial intelligence module can evaluate implemented solutions for a number of different dental practices, including those sharing one or more characteristics or demographics, to determine the suitability and priority of potential solutions for a particular issue.

In various embodiments, method 1000 further comprises a step 1062 of storing trend data within the trend data base 111B. For example, the trend data obtained in step 1060 and used to evaluate the solution can be stored within trend database 111B for further analysis and utilization. Further, some or all of the trend data may be stored in system database 111A.

Figure 13:
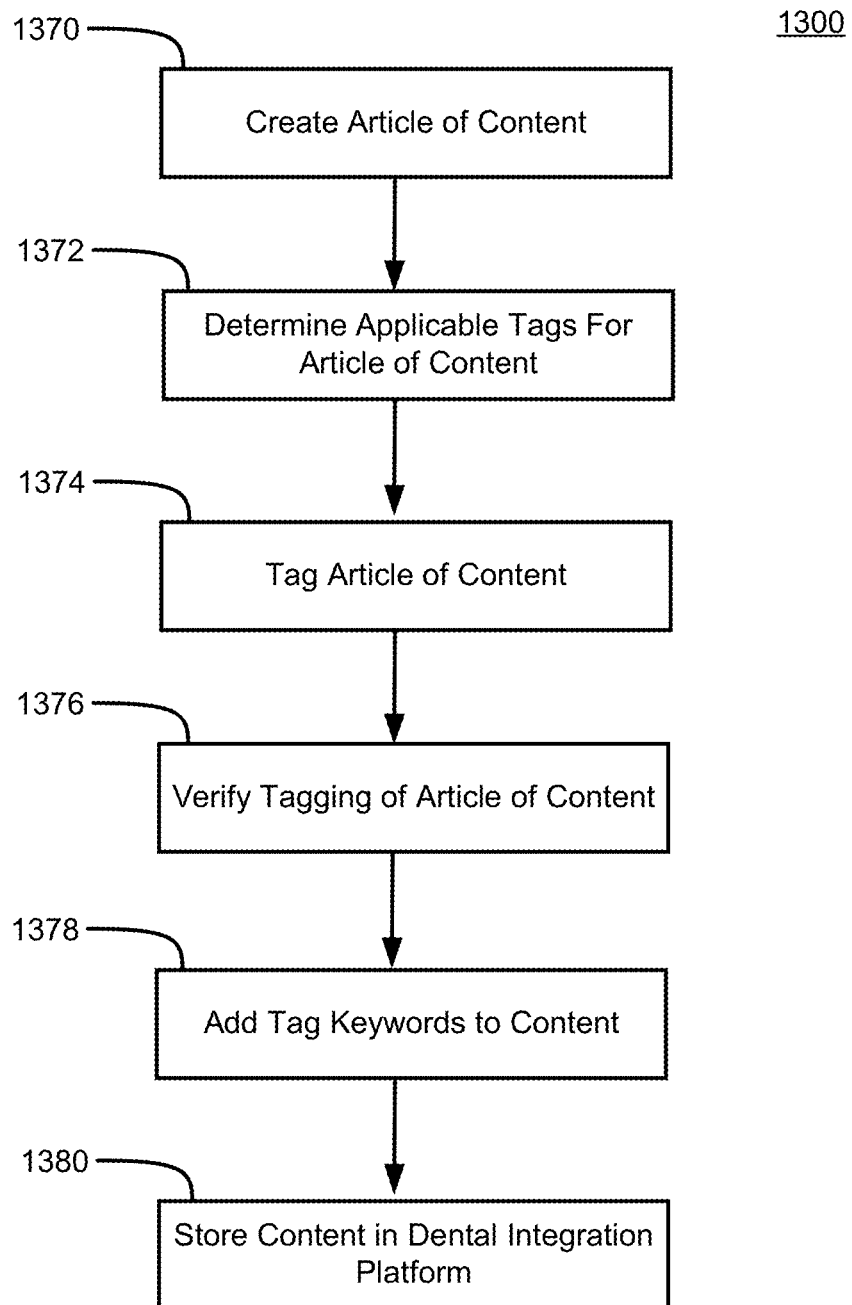
FIG. 13 illustrates a process for managing content relevant to a dental practice, in accordance with various embodiments.

With reference to FIG. 13, a process 1300 for managing content relevant to a dental practice in accordance with various embodiments is illustrated. Process 1300 may, for example, comprise a step 1370 of creating an article of content. In various embodiments, articles of content can comprise information that is educational, instructive, or otherwise informative relating to aspects of the management of dental practices. For example, articles of content can comprise documents, videos, images, audio, or other content providing solutions to issues commonly arising in the management of dental practices and/or administration of dental care. In various embodiments, content created in step 1370 may be stored, among other places, within content module 118.

Figure 14:
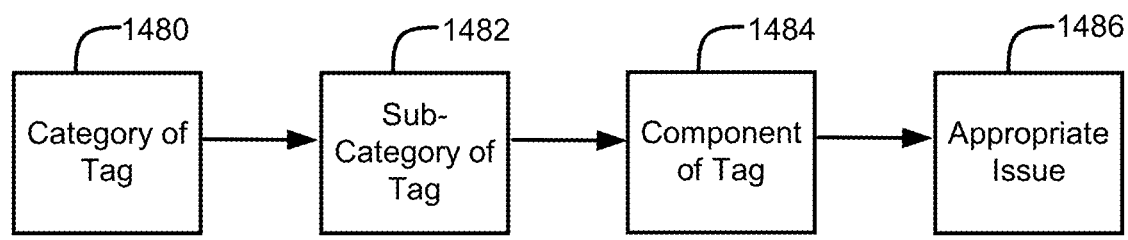
FIG. 14 illustrates a sub-process for tagging content relevant to a dental practice, in accordance with various embodiments.

In various embodiments, process 1300 further comprises a step 1372 of determining applicable tags for an article of content. For example, an article of content created in step 1370 can be evaluated to determine one or more applicable tags based upon the information contained in the article of content. With reference to FIGS. 13 and 14, an exemplary step 1372 for determining appropriate tags for articles of content in accordance with various embodiments is illustrated. The content may be ingested and reviewed by content module 118 of DIP 108 to identify tags associated with the content. For example, content module 118 may use voice recognition to detect the words present in an educational video. The words present in the video may be counted to generate a fingerprint of the most common terms based on the proportional use of the common terms. The proportional use may be used to look up appropriate tags in a lookup table. Additionally, content module 118 may accept user input to allow users to input desired tags associated with each article of content.

In various embodiments, step 1372 comprises a sub-step 1480 of determining an appropriate category of an applicable tag. For example, sub-step 1480 may comprise analyzing the information contained in the article of content to determine the appropriate category under which the article of content should be classified. In various embodiments, the category under which the article of content is classified is the broadest aspect of the organizational structure of the tag. For example, appropriate categories may include data and process optimization, education, technology, and business, among others. After determining the appropriate category, the category is added as a part of the tag.

Step 1372 may further comprise a sub-step 1482 of determining an appropriate sub-category of an applicable tag. In various embodiments, a tag may be classified under one or more sub-categories. For example, a tag may be classified under one or two sub-categories. In various embodiments, sub-categories may include clinical, financial, operational, sales, and platform sub-categories. After determining the appropriate sub-categories, the sub-categories are added as a part of the tag.

In various embodiments, step 1372 further comprises a step 1484 of determining an appropriate component of an applicable tag. For example, a tag may be further classified by a component which corresponds to a specific component of a DIP. Stated another way, the component under which the article of content is classified may comprise one or more modules, components, or applications within a DIP, such as DIP 108 (of FIG. 1A). In various embodiments, an appropriate component may comprise production, projected revenue, hygiene, patient base, messaging, accounts receivable, task manager, scheduling, and treatment planning, among others. After determining the appropriate components, the components are added as a part of the tag.

Step 1372 may further comprise a sub-step 1486 of determining an appropriate issue of an applicable tag. In various embodiments, a tag is further classified (beyond a category, sub-category, and component) as relating to one or more specific issues. For example, a tag may be classified as relating to one or more issues including profit, production (dental hygiene production and/or doctor production), case acceptance, schedule, human resources, policies and procedures, and collections, among others. For example, sub-step 1486 comprises evaluating the information contained in the article of content to determine the appropriate issues under which a tag should be further classified. After determining the appropriate issues, the issues are added as a part of the tag.

In various embodiments, step 1372 comprises creating a tag matrix, into which the appropriate categories, sub-categories, components, and issues are stored.

With reference back to FIG. 13, process 1300 can further comprise a step 1374 of tagging the article of content with one or more appropriate tags. In various embodiments, step 1374 comprises applying the tag or tags determined in step 1372 to the article of content. For example, the article of content may comprise a footer, into which the tagging matrix of step 1372 is inserted. However, any manner of associating the tag with the article of content is within the scope of the present disclosure.

In various embodiments, process 1300 comprises a step 1376 of verifying tagging of an article of content. For example, an administrator or system user of the DIP can verify that the tag or tags generated and applied by steps 1372 and 1374 were properly applied to the article of content.

Process 1300 may further comprise, for example, a step 1378 of adding one or more content key words to the article of content. In various embodiments, content key words can comprise single words or short phrases which accurately describe one or more qualities of the information contained in the article of content.

In various embodiments, process 1300 further comprises a step 1380 of storing content in dental practice management system. For example, the article of content tagged in steps 1370-1378 may be stored within DIP 108. In various embodiments, the article of content is stored within content module 118. In other embodiments, the article of content is stored within formatted database 111. Any manner of storing tagged articles of content within DIP 108 is within the scope of the present disclosure.

Figure 15:
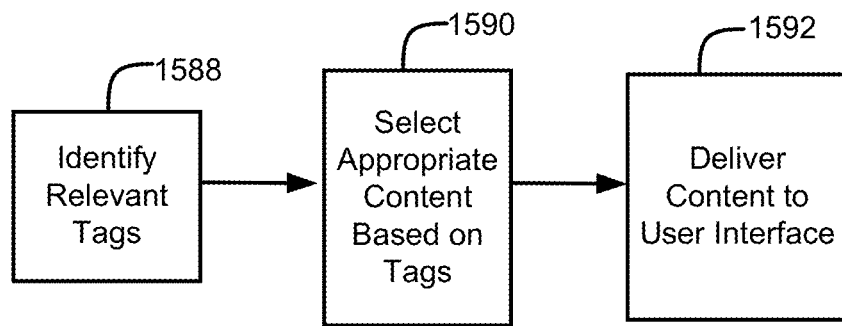
FIG. 15 illustrates a process for providing relevant tagged content to a dental practice, in accordance with various embodiments.

With reference to FIGS. 1A and 15, a process 1500 for providing relevant tagged content to a dental practice in accordance with various embodiments is illustrated. Process 1500 may, for example, comprise a step 1588 of identifying relevant tags. In various embodiments, step 1588 comprises identifying one or more applicable tags within data, such as first user data transmitted from first user system 102 to DIP 108.

For example, step 1588 may comprise the, by the content module, analyzing first user data to identify applicable tags. In various embodiments, first user data is analyzed to determine the presence of a potential issue, problem, area of improvement, or other educational opportunity which correspond to a category, sub-category, component, issue, or key words, such as those described in connection with process 1300. The user data, which is derived from an individual dental practice, may be compared to a model of data derived from similar dental practices to identify shortcomings and/or areas for improvement. For example, if the comparison indicates that the individual dental practice is converting a low rate of clients from the planning treatment phase to the completed treatment phase, then the conversion rate may be an area of deficiency. A lookup table containing tags associated with each potential deficiency may be stored in formatted database 111 and/or content module 118. DIP 108 may use the lookup table to identify relevant tags in response to the identified shortcoming.

In various embodiments, similar dental practices may include practices having one or more characteristics (e.g., demographics) in common with the dental practice utilizing first user system 102. For example, similar dental practices may comprise those operating in geographic locations having similar population and/or economics, past performance metric such as number of patients or annual revenue collected, or any other characteristic that may be quantitatively compared to the dental practice of first user system 102.

In various embodiments, process 1500 further comprises a step 1590 of selecting one or more appropriate articles of content based on tags. For example, step 1590 may comprise locating one or more articles of content, stored in content module 118 and/or formatted database 111, which correspond to the tags identified in step 1588. In various embodiments, step 1590 may also comprise selecting articles of content which contain key words corresponding to the tags identified in step 1588. For example, DIP 108 may select content from formatted database 111 using a query using the identified tags and/or key words associated with the content as criteria for the query.

Process 1500 may further comprise, for example, a step 1592 of delivering the articles of content to a dental practice. For example, one or more articles of content identified in step 1590 may be transmitted by DIP 108 to first user system 102. In various embodiments, the articles of content are transmitted by application server 113 of DIP 108. The articles of content may be displayed on a user interface along with quantitative and qualitative analysis relating to the dental practice. For example, an interaction point on an interface may be displayed along with a dashboard identifying a possible shortcoming and proposing educational content to improve the practitioner in the identified areas.

In various embodiments, step 1592 can comprise a review of the articles identified in step 444 prior to transmitting the content to first user system 102. For example, a consultant utilizing consultant interface 109 may review the content identified in step 1590 to determine if the content is relevant and potentially beneficial to the dental practice utilizing first user system 102. Such review and approval may act as a quality assurance/quality control check on the content delivery mechanism.

In various embodiments, appropriate content can be selected by consultant interface 109. For example, consultant interface 109 can identify one or more issues based on analysis of first user data transmitted from first user interface 115. In various embodiments, a consultant utilizing consultant user system can search content module 118 for content relating to the issue identified with the dental practice of first user system 102. For example, the consultant can search content module 118 using key words related to the issue identified with the dental practice of first user interface 115. After identifying appropriate content, the consultant utilizing consultant interface 109 can instruct application server 113 to deliver the content to first user interface 115.

DIP 108 may, for example, be configured to evaluate the effectiveness of content provided to users, such as the dental practice of first user system 102. In various embodiments, DIP 108 comprises a correlation application running within content module 118 and/or data processing module 112. For example, the correlation application may evaluate a specific criteria of a dental practice (e.g., revenue collection) after the delivery of content identified as relevant and potentially beneficial to the specific criteria. In various embodiments, the correlation application can determine if the specific criteria has improved, and by how much, over a specified time frame after delivery of the content. Further, the correlation application may, for example, compare the change in the specific criteria over the specified time frame to a change in the same specific criteria over the same time frame in one or more peer dental practices. Stated another way, the correlation application can evaluate if revenue collection improved after delivery of content related to improving revenue collection, for example. In various embodiments, the improvement in the specific criteria (such as revenue collection) may be recorded as a measure of the potential effectiveness of the content delivered to the dental practice.

Systems, methods and computer program products are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., WINDOWS®, OS2, UNIX®, LINUX®, SOLARIS®, MacOS, etc.) as well as various conventional support software and drivers typically associated with computers.

The present system or any part(s) or function(s) thereof may be implemented using hardware, software or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations. Useful machines for performing the various embodiments include general purpose digital computers or similar devices.

In fact, in various embodiments, the embodiments are directed toward one or more computer systems capable of carrying out the functionality described herein. The computer system includes one or more processors, such as processor. The processor is connected to a communication infrastructure (e.g., a communications bus, cross over bar, or network). Various software embodiments are described in terms of this exemplary computer system. After reading this description, it will become apparent to a person skilled in the relevant art(s) how to implement various embodiments using other computer systems and/or architectures. Computer system can include a display interface that forwards graphics, text, and other data from the communication infrastructure (or from a frame buffer not shown) for display on a display unit.

The computer system also includes a main memory, such as for example random access memory (RAM), and may also include a secondary memory. The secondary memory may include, for example, a hard disk drive and/or a removable storage drive, representing a floppy disk drive, a magnetic tape drive, an optical disk drive, etc. The removable storage drive reads from and/or writes to a removable storage unit in a well-known manner. Removable storage unit represents a floppy disk, magnetic tape, optical disk, etc. which is read by and written to by removable storage drive. As will be appreciated, the removable storage unit includes a computer usable storage medium having stored therein computer software and/or data.

In various embodiments, secondary memory may include other similar devices for allowing computer programs or other instructions to be loaded into computer system. Such devices may include, for example, a removable storage unit and an interface. Examples of such may include a program cartridge and cartridge interface (such as that found in video game devices), a removable memory chip (such as an erasable programmable read only memory (EPROM), or programmable read only memory (PROM)) and associated socket, and other removable storage units and interfaces, which allow software and data to be transferred from the removable storage unit to computer system.

The computer system may also include a communications interface. Communications interface allows software and data to be transferred between computer system and external devices. Examples of communications interface may include a modem, a network interface (such as an Ethernet card), a communications port, a Personal Computer Memory Card International Association (PCMCIA) slot and card, etc. Software and data transferred via communications interface are in the form of signals which may be electronic, electromagnetic, and optical or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

The terms "computer program medium" and "computer usable medium" and "computer readable medium" are used to generally refer to media such as removable storage drive and a hard disk installed in hard disk drive. These computer program products provide software to computer system.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

In various embodiments, software may be stored in a computer program product and loaded into computer system using removable storage drive, hard disk drive or communications interface. The control logic (software), when executed by the processor, causes the processor to perform the functions of various embodiments as described herein. In various embodiments, hardware components such as application specific integrated circuits (ASICs). Implementation of the hardware state machine so as to perform the functions described herein will be apparent to persons skilled in the relevant art(s).

A web client may be installed on the various computing devices described herein, which may include any device (e.g., personal computer) which communicates via any network, for example such as those discussed herein. Such browser applications comprise Internet browsing software installed within a computing unit or a system to conduct online transactions and/or communications. These computing units or systems may take the form of a computer or set of computers, although other types of computing units or systems may be used, including laptops, notebooks, tablets, hand held computers, personal digital assistants, set-top boxes, workstations, computer-servers, main frame computers, mini-computers, PC servers, pervasive computers, network sets of computers, personal computers, such as IPADS®, IMACS®, and MACBOOKS®, kiosks, terminals, point of sale (POS) devices and/or terminals, televisions, or any other device capable of receiving data over a network. A web-client may run MICROSOFT® INTERNET EXPLORER®, MOZILLA® FIREFOX®, GOOGLE® CHROME®, APPLE® Safari, or any other of the myriad software packages available for browsing the internet.

Practitioners will appreciate that a web client may or may not be in direct contact with an application server. For example, a web client may access the services of an application server through another server and/or hardware component, which may have a direct or indirect connection to an Internet server. For example, a web client may communicate with an application server via a load balancer. In various embodiments, access is through a network or the Internet through a commercially-available web-browser software package.

As those skilled in the art will appreciate, a web client includes an operating system (e.g., WINDOWS®/CE/Mobile, OS2, UNIX®, LINUX®, SOLARIS®, MacOS, etc.) as well as various conventional support software and drivers typically associated with computers. A web client may include any suitable personal computer, network computer, workstation, personal digital assistant, cellular phone, smart phone, minicomputer, mainframe or the like. A web client can be in a home or business environment with access to a network. In various embodiments, access is through a network or the Internet through a commercially available web-browser software package. A web client may implement security protocols such as Secure Sockets Layer (SSL) and Transport Layer Security (TLS). A web client may implement several application layer protocols including http, https, ftp, and sftp.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® APPLE®ts, JAVASCRIPT, active server pages (ASP), common gateway interface scripts (CGI), extensible markup language (XML), dynamic HTML, cascading style sheets (CSS), AJAX (Asynchronous JAVASCRIPT And XML), helper applications, plug-ins, and the like. A server may include a web service that receives a request from a web server, the request including a URL and an IP address (123.56.192.234). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. See, e.g., Alex Nghiem, IT Web Services: A Roadmap for the Enterprise (2003), hereby incorporated by reference.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand. For more information regarding cloud computing, see the NIST's (National Institute of Standards and Technology) definition of cloud computing at http://csrc.nist.gov/publications/nistpubs/800-145/SP800-145.pdf (last visited June 2012), which is hereby incorporated by reference in its entirety.

As used herein, "transmit" may include sending electronic data from one system component to another over a network connection. Additionally, as used herein, "data" may include encompassing information such as commands, queries, files, data for storage, and the like in digital or any other form.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT, VBScript, Macromedia Cold Fusion, COBOL, MICROSOFT® Active Server Pages, assembly, PERL, PHP, awk, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "JAVA® Cryptography" by Jonathan Knudson, published by O'Reilly & Associates (1998); (3) "Cryptography & Network Security: Principles & Practice" by William Stallings, published by Prentice Hall; all of which are hereby incorporated by reference.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Although the disclosure includes a method, it is contemplated that it may be embodied as computer program instructions on a tangible computer-readable carrier, such as a magnetic or optical memory or a magnetic or optical disk. All structural and/or functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

Embodiments

A method comprising: creating an article of content relevant to a dental practice; determining at least one tag for the article of content; tagging the article of content with the at least one tag; verifying the tagging of the article of content; adding at least one key word related to the at least one tag to the article of content; and storing the article of content in a dental integration platform (DIP).

The above-method further comprising identifying a shortcoming of the dental practice by comparing the dental practice to similar dental practices; and transmitting, by the DIP, the article of content to the dental practice in response to identifying the shortcoming.

The above-method, wherein the DIP comprises an application configured to receive a first user data and identify an applicable tag within the first user data. The above-method, wherein the application is executed by a content module.

The above-method, wherein the step of determining at least one tag for the article of content comprises determining an appropriate category of the at least one tag; determining an appropriate sub-category within the appropriate category of the at least one tag; determining an appropriate component of the at least one tag; and determining an appropriate issue of the at least one tag.

The above-method, wherein the article of content is stored within the content module.

A computer-based system, comprising: a first user system in communication with a dental integration platform (DIP), the DIP comprising a database and a content module, wherein the first user system associated with a dental practice is configured to transmit a first user data to the DIP, wherein the first user data is stored in the database, wherein the content module comprises a processor and a tangible, non-transitory memory configured to communicate with the processor and having instructions stored thereon, the content module configured, upon execution of the instructions by the processor, to: identify at least one of an applicable tag and an applicable key word from the first user data stored in the database; identify an article of content comprising at least one of the applicable tag and the applicable key word; and transmit the article of content to a first user interface.

The above-system, further comprising a consultant interface in communication with the DIP and configured to instruct the DIP to transmit the article of content to the first user interface.

The above-system, further comprising a data transmitting module configured to receive data from the first user system.

The above-system, wherein the content module is further configured to determine an appropriate category of the tag; determine an appropriate sub-category within the appropriate category of the tag; determine an appropriate component of the tag; and determine an appropriate issue of the tag.

The above-system, wherein the article of content is stored within the content module.

An article of manufacture including a non-transitory, tangible computer readable storage medium having instructions stored thereon that, in response to execution by a computer-based system, cause a content module of a dental practice management system (DIP) to perform operations comprising: determining at least one tag for an article of content stored within the DIP; tagging the article of content with the at least one tag; verifying the tagging of the article of content; and adding at least one key word related to the at least one tag to the article of content.

The above-article of manufacture, wherein the content module is further configured to transmit the article of content to a dental practice in response to identifying a shortcoming of the dental practice.

The above-article of manufacture, wherein the content module is further configured to receive a first user data and identify an applicable tag within the first user data.

The above-article of manufacture, wherein determining at least one tag for the article of content comprises: determining an appropriate category of the tag; determining an appropriate sub-category within the appropriate category of the tag; determining an appropriate component of the tag; and determining an appropriate issue of the tag.

The above-article, wherein the article of content is stored within the content module.

What is claimed is:
1. A method comprising:
receiving, by a processor, a first user data from a first user system associated with a dental practice;
converting, by the processor using a data transmitting module, the first user data in a first format to a second common format with a plurality of dental practices, by mapping fields of the first user data into a schema that supports the second common format;
processing, by the processor, the first user data to create dental treatment data comprising a dental treatment plan with dental service codes for each patient of the first user data, wherein the dental treatment plan includes dental hygiene procedures, recommended dental treatments and dates for scheduling the recommended dental treatments;
determining, by the processor, scheduling efficiency data by comparing potential revenue from the dental hygiene procedures and the recommended dental treatments with total dental treatments accepted, total dental treatments scheduled, total dental treatments completed and total dental treatments performed;
creating, by the processor, scheduling data comprising a daily schedule of dental treatments to be performed by each employee of the dental practice;
comparing, by the processor, the scheduling data of the dental practice with scheduling data of a plurality of dental practices sharing one or more characteristics with the dental practice;
creating, by the processor, suggestions for improvement in practice management and practical skills involving hygiene based on the comparing of the scheduling data;
formatting, by the processor using an application server, the dental treatment data and scheduling efficiency data for transmittal to a first user interface;
creating, by the processor, a schedule model based on the dental treatment data of a plurality of dental practices sharing one or more characteristics with the dental practice;
comparing, by the processor, the dental treatment data and the scheduling efficiency data with the schedule model;
filtering, by the processor, patient and financial data from the first user data;
generating, by the processor, financial projections for the dental practice based on financial factors and the patient and financial data;
generating, by the processor, a financial model from the patient and financial data and the financial projections based on the plurality of dental practices in a local geographic area;
selecting, by the processor, and based on the schedule model and the financial model, an operational issue from an issue database using the quantifiable metric to identify the operational issue, wherein the operational issue comprises an issue profile, wherein the issue profile comprises the quantifiable metric in response to the quantifiable metric being below a threshold value;
tagging, by the processor, an article of content related to the operational issue, wherein the article of content includes dental clinical content including hygiene;
adding, by the processor, a content key word to the article of content;
identifying, by the processor, a solution corresponding with the issue profile, wherein the solution comprises the article of content;
confirming, by the processor, the solution;
receiving, by the processor, an indication that the confirmed solution is implemented;
evaluating, by the processor using a machine learning module, an effectiveness of the confirmed solution by analyzing trend data for the quantifiable metric for a period after the confirmed solution is implemented in a plurality of dental practices sharing one or more characteristics with the dental practice; and modifying, by the processor, the solution based on the trend data from evaluating the effectiveness of the confirmed solution.

2. The method of claim 1, wherein the confirming the solution comprises transmitting, by a dental integration platform (DIP), the solution to a consultant user interface and receiving, from the consultant user interface, a confirmation from a consultant for the solution.

3. The method of claim 1, wherein the confirming the solution comprises, by at least one of a machine learning module or an artificial intelligence module, instructing the first user system to implement the solution.

4. The method of claim 1, wherein the quantifiable metric comprises at least one of a projected financial data, an acceptance rate data, a completion rate data, a potential revenue of planned to accepted dental treatments data, a percentage revenue of accepted to scheduled dental treatments data, a potential revenue of scheduled to completed dental treatments data, and a percentage revenue of accepted to completed dental treatments data.

5. The method of claim 1, wherein the financial projections comprise a projected dental treatment revenue, a projected accepted revenue, a projected completed revenue, and expense data for a predetermined time period.

6. The method of claim 1, wherein the financial model comprises an average annual potential revenue, an average annual accepted revenue, an average completed revenue, expense data, an average $T_{PA}$, an average $T_{AS}$, an average $T_{SC}$, and an average $T_{PC}$ of the plurality of dental practices.

7. The method of claim 1, further comprising determining, by the processor via the consultant user interface, a subset of data that is transmitted to the first user interface.

8. The method of claim 1, wherein the financial factors are generated from potential revenue of the planned dental treatment to the accepted dental treatment ($\$R_{PA}$), a percentage revenue of the planned dental treatment to the accepted dental treatment (% $R_{PA}$), a potential revenue of the accepted dental treatment to the scheduled dental treatment ($\$R_{AS}$), a potential revenue of the scheduled dental treatment to the completed dental treatment ($\$R_{SC}$), and a percentage revenue of the accepted dental treatment to the completed dental treatment (% $R_{AC}$).

9. The method of claim 1, further comprising storing, by the processor, the first user data in at least one of a relational database comprising various tables related by keys, a non-relational database or a hybrid database.

10. The method of claim 1, wherein the financial model comprises an average of an actual revenue collected of each of the plurality of dental practices having the predetermined characteristics.

11. The method of claim 1, wherein the schedule model comprises at least one of an average time of accepting a dental treatment and an average time of completing a dental treatment of each of the plurality of dental practices having the predetermined characteristics.

12. The method of claim 1, wherein the solution comprises at least one of a document, video, image or audio.

13. The method of claim 1, wherein the trend data is stored within a trend database of a dental integration platform (DIP).

14. The method of claim 1, wherein the trend data is captured at an interval of at least one of 30 days, 60 days, 90 days, or 120 days.

15. The method of claim 1, wherein the solution is communicated to a first user via the first user interface.

16. The method of claim 1, wherein the scheduling model comprises comprising an average time period from a planned dental treatment to an accepted dental treatment ($T_{PA}$), an average time period from the accepted dental treatment to a scheduled dental treatment ($T_{AS}$), an average time period from the scheduled dental treatment to a completed dental treatment ($T_{SC}$), and an average time period from the planned dental treatment to the completed dental treatment ($T_{PC}$).

17. The method of claim 1, further comprising instructing a dental integration platform (DIP) to transmit the financial projections and the scheduling data to the first user interface.

18. The method of claim 1, further comprising transmitting, by the processor using an application server, at least one of the dental treatment data, financial projections, scheduling efficiency data, scheduling data, suggestions for improvement, financial projections or solution to the first user interface.

19. An article of manufacture including a non-transitory, tangible computer readable storage medium having instructions stored thereon that, in response to execution by a computer-based system, cause the computer-based system to perform operations comprising:

receiving, by the processor, a first user data from a first user system associated with a dental practice;

converting, by the processor using a data transmitting module, the first user data in a first format to a second common format with a plurality of dental practices, by mapping fields of the first user data into a schema that supports the second common format;

processing, by the processor, the first user data to create dental treatment data comprising a dental treatment plan with dental service codes for each patient of the first user data, wherein the dental treatment plan includes dental hygiene procedures, recommended dental treatments and dates for scheduling the recommended dental treatments;

determining, by the processor, scheduling efficiency data by comparing potential revenue from the dental hygiene procedures and the recommended dental treatments with total dental treatments accepted, total dental treatments scheduled, total dental treatments completed and total dental treatments performed;

creating, by the processor, scheduling data comprising a daily schedule of dental treatments to be performed by each employee of the dental practice;

comparing, by the processor, the scheduling data of the dental practice with scheduling data of a plurality of dental practices sharing one or more characteristics with the dental practice;

creating, by the processor, suggestions for improvement in practice management and practical skills involving hygiene based on the comparing of the scheduling data;

formatting, by the processor using an application server, the dental treatment data and scheduling efficiency data for transmittal to a first user interface;

creating, by the processor, a schedule model based on the dental treatment data of a plurality of dental practices sharing one or more characteristics with the dental practice;

comparing, by the processor, the dental treatment data and the scheduling efficiency data with the schedule model;

filtering, by the processor, patient and financial data from the first user data;

generating, by the processor, financial projections for the dental practice based on financial factors and the patient and financial data;

generating, by the processor, a financial model from the patient and financial data and the financial projections based on the plurality of dental practices in a local geographic area;

selecting, by the processor, and based on the schedule model and the financial model, an operational issue from an issue database using the quantifiable metric to identify the operational issue, wherein the operational issue comprises an issue profile, wherein the issue profile comprises the quantifiable metric in response to the quantifiable metric being below a threshold value;

tagging, by the processor, an article of content related to the operational issue, wherein the article of content includes dental clinical content including hygiene;

adding, by the processor, a content key word to the article of content;

identifying, by the processor, a solution corresponding with the issue profile, wherein the solution comprises the article of content;

confirming, by the processor, the solution;

receiving, by the processor, an indication that the confirmed solution is implemented;

evaluating, by the processor using a machine learning module, an effectiveness of the confirmed solution by analyzing trend data for the quantifiable metric for a period after the confirmed solution is implemented in a plurality of dental practices sharing one or more characteristics with the dental practice; and modifying, by the processor, the solution based on the trend data from evaluating the effectiveness of the confirmed solution.

20. A system comprising:

a processor; and a tangible, non-transitory memory configured to communicate with the processor, the tangible, non-transitory memory having instructions stored thereon that, in response to execution by the processor, cause the processor to perform operations comprising:

receiving, by the processor, a first user data from a first user system associated with a dental practice;

converting, by the processor using a data transmitting module, the first user data in a first format to a second common format with a plurality of dental practices, by mapping fields of the first user data into a schema that supports the second common format;

processing, by the processor, the first user data to create dental treatment data comprising a dental treatment plan with dental service codes for each patient of the first user data, wherein the dental treatment plan includes dental hygiene procedures, recommended dental treatments and dates for scheduling the recommended dental treatments;

determining, by the processor, scheduling efficiency data by comparing potential revenue from the dental hygiene procedures and the recommended dental treatments with total dental treatments accepted, total dental treatments scheduled, total dental treatments completed and total dental treatments performed;

creating, by the processor, scheduling data comprising a daily schedule of dental treatments to be performed by each employee of the dental practice;

comparing, by the processor, the scheduling data of the dental practice with scheduling data of a plurality of dental practices sharing one or more characteristics with the dental practice;

creating, by the processor, suggestions for improvement in practice management and practical skills involving hygiene based on the comparing of the scheduling data;

formatting, by the processor using an application server, the dental treatment data and scheduling efficiency data for transmittal to a first user interface;

creating, by the processor, a schedule model based on the dental treatment data of a plurality of dental practices sharing one or more characteristics with the dental practice;

comparing, by the processor, the dental treatment data and the scheduling efficiency data with the schedule model;

filtering, by the processor, patient and financial data from the first user data;

generating, by the processor, financial projections for the dental practice based on financial factors and the patient and financial data;

generating, by the processor, a financial model from the patient and financial data and the financial projections based on the plurality of dental practices in a local geographic area;

selecting, by the processor, and based on the schedule model and the financial model, an operational issue from an issue database using the quantifiable metric to identify the operational issue, wherein the operational issue comprises an issue profile, wherein the issue profile comprises the quantifiable metric in response to the quantifiable metric being below a threshold value;

tagging, by the processor, an article of content related to the operational issue, wherein the article of content includes dental clinical content including hygiene;

adding, by the processor, a content key word to the article of content;

identifying, by the processor, a solution corresponding with the issue profile, wherein the solution comprises the article of content;

confirming, by the processor, the solution;

receiving, by the processor, an indication that the confirmed solution is implemented;

evaluating, by the processor using a machine learning module, an effectiveness of the confirmed solution by analyzing trend data for the quantifiable metric for a period after the confirmed solution is implemented in a plurality of dental practices sharing one or more characteristics with the dental practice; and modifying, by the processor, the solution based on the trend data from evaluating the effectiveness of the confirmed solution.

\* \* \* \* \*